United States Patent
Umezawa et al.

(10) Patent No.: US 10,578,588 B2
(45) Date of Patent: Mar. 3, 2020

(54) PHOTOACOUSTIC APPARATUS, INFORMATION PROCESSING METHOD, AND STORAGE MEDIUM

(71) Applicant: CANON KABUSHIKI KAISHA, Tokyo (JP)

(72) Inventors: Kohtaro Umezawa, Tokyo (JP); Ryuichi Nanaumi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 179 days.

(21) Appl. No.: 15/716,075

(22) Filed: Sep. 26, 2017

(65) Prior Publication Data

US 2018/0088086 A1  Mar. 29, 2018

(30) Foreign Application Priority Data

Sep. 27, 2016  (JP) ................... 2016-188417

(51) Int. Cl.
*G01N 33/00* (2006.01)
*G01N 29/24* (2006.01)

(52) U.S. Cl.
CPC ..... *G01N 29/2418* (2013.01); *G01N 33/0036* (2013.01)

(58) Field of Classification Search
CPC .. A61B 5/0095; A61B 5/145; G01N 29/2418; G01N 33/0036
USPC ........................................................ 73/645
See application file for complete search history.

(56) References Cited

U.S. PATENT DOCUMENTS

| 8,977,337 B2 * | 3/2015 | Oyama | A61B 5/0095 600/407 |
| 9,339,254 B2 * | 5/2016 | Wanda | A61B 5/14542 |
| 2013/0188707 A1 * | 7/2013 | Shimizu | H04N 19/597 375/240.12 |

(Continued)

FOREIGN PATENT DOCUMENTS

| EP | 2749209 A1 | 7/2014 |
| EP | 2954839 A1 | 12/2015 |

(Continued)

OTHER PUBLICATIONS

Minghua Xu, et al.; Universal back-projection algorithm for photoacoustic computed tomography; Physical Review E; Jan. 19, 2005; pp. (016706-1-016706-7); American Physical Society; College Park, Maryland, USA.

(Continued)

*Primary Examiner* — Jacques M Saint Surin
(74) *Attorney, Agent, or Firm* — Canon U.S.A., Inc. I.P. Division

(57) ABSTRACT

A photoacoustic apparatus comprising a processing unit configured to obtain first image data corresponding to a first wavelength, obtain second image data corresponding to a second wavelength different from the first wavelength, perform normalization processing on at least one of the first image data and the second image data so as to decrease a difference in an image characteristic between the first image data and the second image data, and obtain position shift information associated with irradiation timing of the light having the first and second wavelengths on the basis of the first and second image data at least one of which is subjected to the normalization processing.

15 Claims, 15 Drawing Sheets

(56) References Cited

U.S. PATENT DOCUMENTS

| | | | | |
|---|---|---|---|---|
| 2014/0202247 A1* | 7/2014 | Kasamatsu | ............ | H01S 3/105 |
| | | | | 73/579 |
| 2015/0057534 A1* | 2/2015 | Tsujita | ................ | A61B 5/0095 |
| | | | | 600/425 |
| 2018/0084997 A1* | 3/2018 | Umezawa | ............ | A61B 5/0035 |

FOREIGN PATENT DOCUMENTS

| | | | |
|---|---|---|---|
| JP | 2014140716 A | | 8/2014 |
| JP | 2016019847 A | | 2/2016 |
| KR | 10-2015-0121872 A | | 10/2015 |
| WO | 2012137855 A1 | | 10/2012 |
| WO | 2013188707 A1 | | 12/2013 |
| WO | 2014115214 A1 | | 7/2014 |

OTHER PUBLICATIONS

Y. Ueda, et al.; Development of optical mammography based on analysis of time-resolved photon path distribution; Proc of SPIE.; 2010; vol. 7561; pp. 756117-1-756117-6; SPIE.; USA.

* cited by examiner

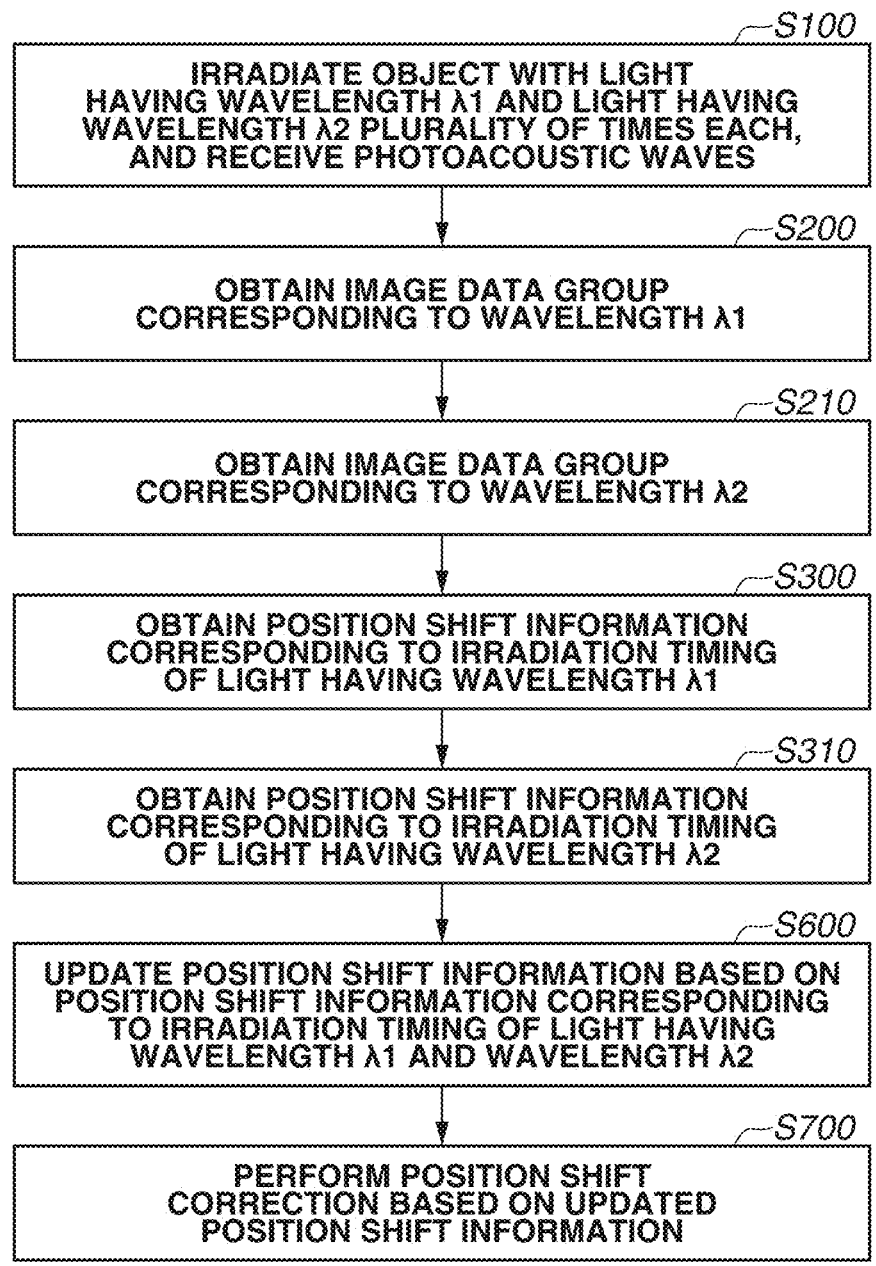

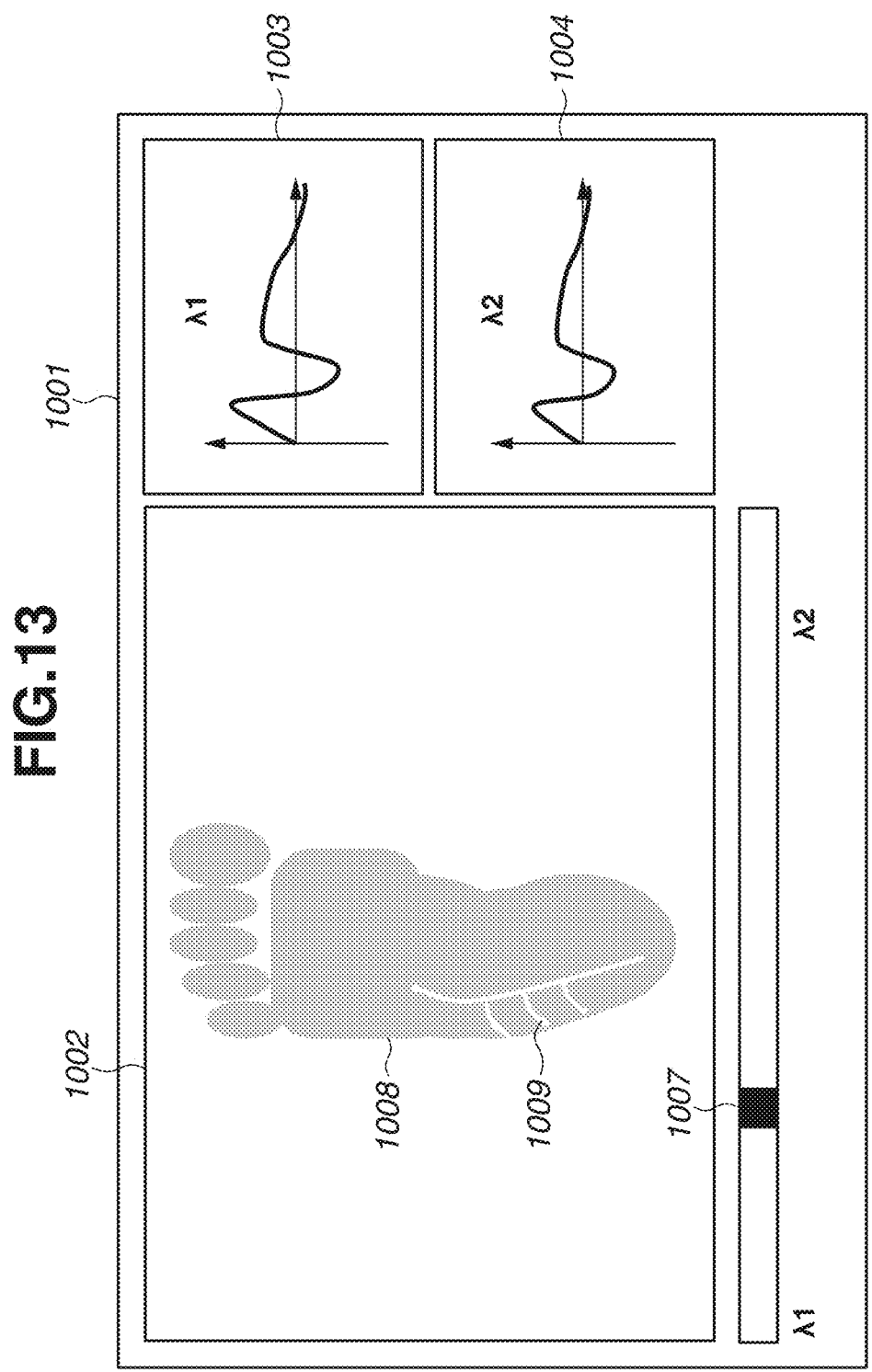

PHOTOACOUSTIC APPARATUS, INFORMATION PROCESSING METHOD, AND STORAGE MEDIUM

BACKGROUND OF THE INVENTION

Field of the Invention

The present invention relates to a photoacoustic apparatus.

Description of the Related Art

In the medical field, imaging of functional information, or physiological information about a living body, has been researched in recent years. There is a photoacoustic imaging (PAI) as one of imaging techniques of functional information.

In PAI, an object is irradiated with light. The irradiation light is propagated and dispersed in the object, and its energy is absorbed into the object. As a result, acoustic waves (hereinafter, referred to photoacoustic waves) are generated by the photoacoustic effect. A reception signal of the photoacoustic waves is analyzed to obtain a spatial distribution of optical characteristic values inside the object as image data.

Suppose that the object is irradiated with light a plurality of times, and image data is generated based on photoacoustic waves generated by the plurality of times of light irradiation. In such a case, if a relative position between the object and a probe varies during the plurality of times of light irradiation, resolution of the image data deteriorates.

Japanese Patent Application Laid-Open No. 2014-140716 discusses a technique in which a position shift amount between a plurality of pieces of image data obtained by a plurality of times of light irradiation is calculated to estimate the amount of variation in the relative position between an object and a probe. Japanese Patent Application Laid-Open No. 2014-140716 also discusses a technique for registering a plurality of pieces of image data based on the estimated amount of variation in the relative position.

In PAI, functional information can be obtained by irradiating an object with light having a plurality of mutually different wavelengths.

However, if a plurality of pieces of image data is generated based on photoacoustic waves generated by irradiation with light having a respective plurality of wavelengths, a position shift may occur between the plurality of pieces of image data.

SUMMARY OF THE INVENTION

The present invention is directed to an apparatus that can estimate position shift information between a plurality of pieces of image data with high accuracy when generating an image data group (plurality of pieces of image data) based on photoacoustic waves generated by light irradiation with a plurality of wavelengths. In other words, the present invention is directed to an apparatus that can estimate the amount of variation in a relative position between an object and a probe even when generating an image data group based on photoacoustic waves generated by light irradiation with a plurality of wavelengths.

According to an aspect of the present invention, a photoacoustic apparatus comprising a processing unit configured to obtain first image data generated based on an acoustic wave generated by irradiating an object with light having a first wavelength, obtain second image data generated based on an acoustic wave generated by irradiating the object with light having a second wavelength different from the first wavelength, perform normalization processing on at least one of the first image data and the second image data so as to decrease a difference in an image characteristic between the first image data and the second image data, and obtain position shift information associated with irradiation timing of the light having the first and second wavelengths on the basis of the first and second image data at least one of which is subjected to the normalization processing.

Further features of the present invention will become apparent from the following description of exemplary embodiments with reference to the attached drawings.

BRIEF DESCRIPTION OF THE DRAWINGS

FIG. 12 is a flowchart illustrating an operation of a photoacoustic apparatus according to a second exemplary embodiment.

FIG. 13 is a diagram illustrating a graphical user interface (GUI) according to the second exemplary embodiment.

DESCRIPTION OF THE EMBODIMENTS

Figure 1:
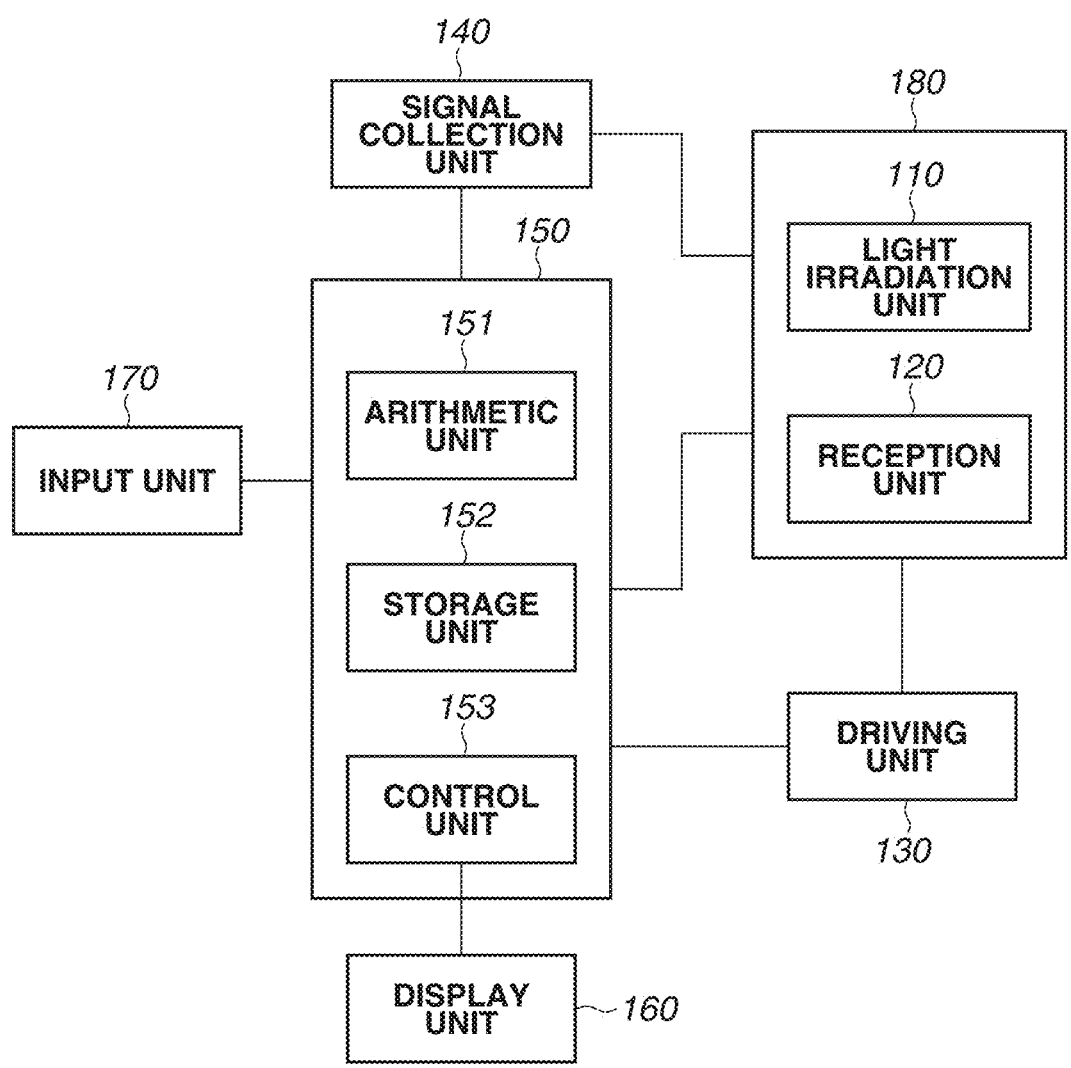
FIG. 1 is a block diagram illustrating a configuration of a photoacoustic apparatus according to a first exemplary embodiment.

Exemplary embodiments of the present invention will be described below with reference to the drawings. Similar components are in principle designated by the same reference numerals. A description thereof will be omitted.

As employed herein, a phenomenon in which a relative position between an object to be imaged and a probe varies will be referred to as a "position shift". The amount of variation in the relative position between the object to be imaged and the probe will be referred to as a "position shift amount". The amount of change in the position of the object to be imaged occurring in an image data group (a plurality of pieces of image data) due to a position shift will be referred to as a "position shift amount between a plurality of pieces of image data". A parameter expressing a position shift such as a translation amount, a rotation amount, and a deformation amount will be referred to as "position shift information".

A position shift occurs if an object moves or a probe moves during a plurality of times of light irradiation. For example, if a user holds and scans a handheld probe or a scanning unit mechanically scans a probe, the probe moves. Such position shifts can result in a drop in resolution when image data is generated based on photoacoustic waves generated by the plurality of times of light irradiation.

The intensity of photoacoustic waves generated by light irradiation is determined in proportion to an absorption coefficient of the object to be imaged. Since the absorption coefficient has a wavelength dependence, the intensity of occurring photoacoustic waves varies with wavelength even if the photoacoustic waves have the same light fluence regardless of the wavelength.

Suppose that a position shift between a plurality of pieces of image data is estimated as discussed in Japanese Patent Application Laid-Open No. 2014-140716. In such a case, the estimation accuracy of the position shift may drop if the plurality of pieces of image data has different image intensities for the same object to be imaged. If a position shift amount is estimated by using an image data group obtained by light irradiation with each of a plurality of mutually different wavelengths, the estimation accuracy of the position shift may drop due to reasons such as a difference in the image intensity or resolution between the wavelengths.

A photoacoustic apparatus according to an exemplary embodiment of the present invention obtains position shift information between a plurality of pieces of image data corresponding to part of a plurality of mutually different wavelengths, and uses the position shift information to obtain position shift information corresponding to the other wavelength(s). Since the position shift information corresponding to the plurality of wavelengths is estimated with reference to the position shift information corresponding to a specific wavelength, the effect of a difference in the image intensity between the wavelengths on the acquisition accuracy of the position shift information can be suppressed. Since the position shift information corresponding to a specific wavelength is obtained to obtain the position shift information corresponding to the other wavelength(s) by interpolation, the amount of processing needed to obtain the position shift information corresponding to the other wavelength(s) can be reduced.

More specifically, in a photoacoustic apparatus according to an exemplary embodiment of the present invention, an object is separately irradiated with light having mutually different first and second wavelengths a plurality of times each. A first image data group corresponding to the first wavelength is then generated, and position shift information between pieces of image data in the first image data group is obtained. The position shift information (first position shift information) obtained here is equivalent to the amount of variation (position shift amount) in the relative position between the object and the probe corresponding to irradiation timing of the light having the first wavelength. Based on the first position shift information, the amount of variation (position shift amount) between the object and the probe corresponding to an irradiation timing of the light having the second wavelength is estimated.

A photoacoustic apparatus according to an exemplary embodiment of the present invention obtains functional information based on position shift information corresponding to light irradiation with a plurality of wavelengths, estimated as described above, and reception data (signal group or image data) resulting from photoacoustic waves generated by the light irradiation with the plurality of wavelengths. Examples of the functional information include information indicating a substance concentration, such as an oxyhemoglobin concentration, a deoxyhemoglobin concentration, a total amount of hemoglobin, and oxygen saturation. The total amount of hemoglobin refers to the total sum of the amounts of oxyhemoglobin and deoxyhemoglobin. The oxygen saturation refers to the rate of oxyhemoglobin relative to total hemoglobin.

The functional information is not limited to image data expressing a spatial distribution, and may be information expressing a numerical value or text. For example, the functional information is a concept including information such as an average concentration of a substance constituting the object, a value of a spatial distribution of a substance concentration at a specific position, and statistic value (average and median) of pixel values in a spatial distribution of a substance concentration. For example, a numerical value of an average concentration of a substance constituting the object may be displayed on a display unit 160 as an image indicating the functional information.

In an exemplary embodiment of the present invention, position shift information may be obtained based on an image data group that is obtained by using light having a wavelength at which the molecular absorption coefficient of oxyhemoglobin and that of deoxyhemoglobin are equal. If the object to be imaged is blood vessels, variations in the image intensity of the blood vessels are small since the intensity of photoacoustic waves produced from the blood vessels by using the light having such a wavelength is independent of oxygen saturation. Thus, the use of the light having such a wavelength tends to increase the estimation accuracy of the position shift information. The estimation accuracy of the position shift information tends to be high not only at the wavelength at which the molecular absorption coefficient of oxyhemoglobin and that of deoxyhemoglobin are exactly equal (isosbestic point), but also at wavelengths at which the molecular absorption coefficients are substantially equal. For example, wavelengths within ±10 nm of the isosbestic point may be employed as the wavelengths at which the molecular absorption coefficients are substantially equal. For example, isosbestic point of oxyhemoglobin and deoxyhemoglobin are equivalent to within 10% of the equal molecular absorption coefficients may be employed as the wavelengths at which the molecular absorption coefficients are substantially equal. In other words, based on position shift information obtained by using light having a wavelength suitable for the acquisition of position shift information, position shift information corresponding to the other wavelength(s) may desirably be obtained.

A configuration and processing of a photoacoustic apparatus according to a first exemplary embodiment will be described below.

The present exemplary embodiment describes an example in which the photoacoustic apparatus is used. The configuration of the photoacoustic apparatus according to the present exemplary embodiment will be described with reference to FIG. 1. FIG. 1 is a schematic block diagram illustrating the entire photoacoustic apparatus. The photoacoustic apparatus according to the present exemplary embodiment includes a driving unit 130, a signal collection unit 140, a computer 150, a display unit 160, an input unit 170, and a probe 180.

Figure 2:
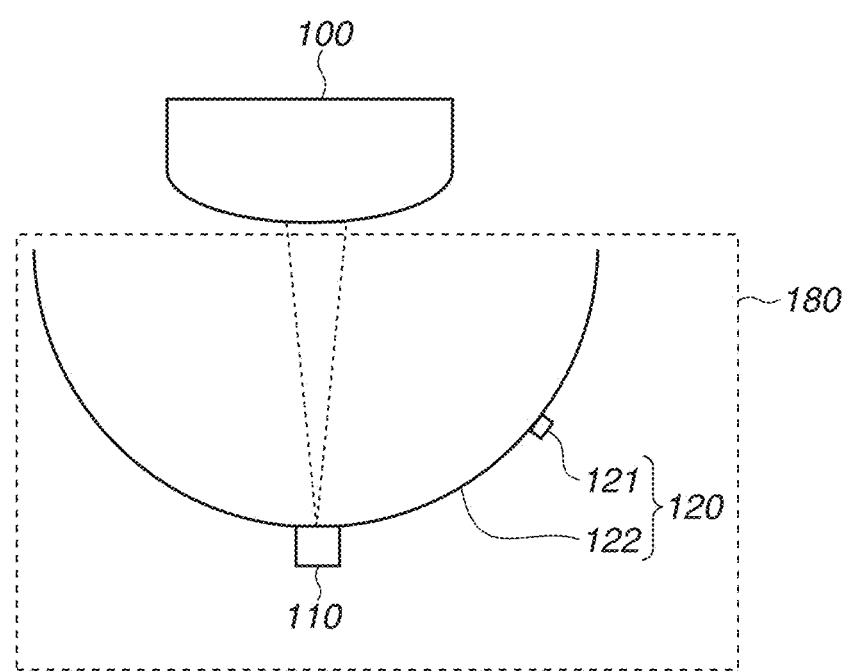
FIG. 2 is a diagram illustrating a probe according to the first exemplary embodiment.

FIG. 2 is a schematic diagram illustrating the probe 180 according to the present exemplary embodiment. The probe 180 includes a light irradiation unit 110 and a reception unit 120. The measurement target is an object 100.

The driving unit 130 drives the light irradiation unit 110 and the reception unit 120 to perform mechanical scanning. The light irradiation unit 110 irradiates the object 100 with pulsed light, and acoustic waves occur inside the object 100. Acoustic waves generated by a photoacoustic effect due to light will be referred to as photoacoustic waves. The reception unit 120 receives the photoacoustic waves to output an electrical signal (photoacoustic signal), which is an analog signal.

The signal collection unit 140 converts the analog signal output from the reception unit 120 into a digital signal, and outputs the digital signal to the computer 150. The computer 150 stores the digital signal output from the signal collection unit 140 as signal data derived from ultrasonic waves or photoacoustic waves.

The computer 150 performs signal processing on the stored digital signal to generate image data expressing a photoacoustic image. The computer 150 applies image processing onto the obtained image data and then outputs the image data to the display unit 160. The display unit 160 displays the photoacoustic image. A doctor or technician as an operator can observe the photoacoustic image displayed on the display unit 160 to carry out a diagnosis. Based on a storage instruction from the operator or the computer 150, the displayed image is stored in a memory in the computer 150 or a data management system connected with the modality via a network.

The computer 150 also performs driving control of the components included in the photoacoustic apparatus. The display unit 160 may display a graphical user interface (GUI) aside from images generated by the computer 150. The input unit 170 is configured so as to allow the operator to input information. By using the input unit 170, the operator can make operations such as to start and end measurement and give instructions to store a generated image.

A photoacoustic image obtained by the photoacoustic apparatus according to the present exemplary embodiment is a concept including all images derived from photoacoustic waves generated by light irradiation. A photoacoustic image is image data expressing a spatial distribution of at least one of a generated sound pressure (initial sound pressure) of photoacoustic waves, an optical absorption energy density, and an optical absorption coefficient.

The components of the photoacoustic apparatus according to the present exemplary embodiment will be described in detail below.

<Light Irradiation Unit 110>

The light irradiation unit 110 includes a light source that emits the pulsed light, and an optical system that guides the pulsed light emitted from the light source to the object 100. The pulsed light may include light of rectangular waves and triangular waves.

The light emitted from the light source may have a pulse width of greater than or equal to 1 ns and less than or equal to 100 ns. The light may have a wavelength in the range of approximately 400 nm to 1600 nm. In a case of imaging blood vessels with high resolution, a wavelength (greater than or equal to 400 nm and less than or equal to 700 nm) at which absorption by the blood vessels is high may be used. In imaging a deep part of a living body, light having a wavelength (greater than or equal to 700 nm and less than or equal to 1100 nm) at which absorption by background tissue (such as water and fat) of the living body is typically low may be used.

A laser or a light-emitting diode may be used as the light source. If light having a plurality of wavelengths is used for measurement, a light source capable of wavelength conversion may be used. If the object 100 is irradiated with light having a plurality of wavelengths, a plurality of light sources that generate light of respective different wavelengths may be provided and alternately used for irradiation. If a plurality of light sources is used, the light sources will be referred to collectively as a light source. Various lasers may be used, including a solid-state laser, a gas laser, a dye laser, and a semiconductor laser. For example, a pulsed laser such as a Nd:YAG laser and an alexandrite laser may be used as the light source. A Ti:Sa laser using Nd:YAG laser light as excitation light, and an optical parametric oscillators (OPO) laser may be used as the light source. A microwave source may be used as the light source.

The optical system may include optical elements such as a lens, a mirror, and an optical fiber. If the object 100 is the breast, a light emission part of the optical system may include a diffusion plate for diffusing light so that the pulsed light is expanded in beam diameter for irradiation. In a case of a photoacoustic microscope, the light emission part of the optical system may include a lens to emit a focused beam for higher resolution.

The light irradiation unit 110 may directly irradiate the object 100 with the pulsed light from the light source without an optical system.

<Reception Unit 120>

The reception unit 120 includes a transducer 121 that receives acoustic waves to output an electrical signal, and a supporting member 122 that supports the transducer 121. The transducer 121 can also transmit acoustic waves. While FIG. 2 illustrates only one transducer 121 for the sake of convenience, the reception unit 120 may include a plurality of transducers.

Members constituting the transducer 121 may be made of piezoelectric ceramic materials typified by lead zirconate titanate (PZT), and polymer piezoelectric film materials typified by polyvinylidene difluoride (PVDF). Elements other than a piezoelectric element may be used. For example, capacitive transducers (capacitive micro-machined ultrasonic transducers (CMUT)) and transducers using a Fabry-Perot interferometer may be used. Any transducer may be employed as long as acoustic waves can be received to output an electrical signal. The signal obtained by the transducer is a time-resolved signal. That is, the amplitude of the signal obtained by transducer indicates a value based on the sound pressure (e.g., a value proportional to the sound pressure) received by the transducer at each time.

Photoacoustic waves typically include frequency components of 100 kHz to 100 MHz. A transducer capable of detecting such frequencies may be employed as the transducer 121.

The supporting member 122 may be made of a metal material having high mechanical strength. The surface of the supporting member 122 on the object 100 side may be mirror-finished or processed to scatter light so as to increase the irradiation light incident on the object 100. In the present exemplary embodiment, the supporting member 122 has the shape of a hemispherical enclosure, and is configured so as to be able to support a plurality of transducers 121 on the hemispherical enclosure. In such a case, the directional axes of the transducers 121 arranged on the supporting member 122 converge to near the center of curvature of the hemisphere. If the signals output from the plurality of transducers 121 are used for imaging, image quality near the center of curvature improves. The supporting member 122 may have any configuration as long as the transducer(s) 121 can be supported. The supporting member 122 may support a plurality of transducers 121 so that the transducers 121 are arranged on a flat surface or curved surface called one-dimensional (1D) array, 1.5-dimensional (1.5D) array, 1.75-dimensional (1.75D) array, or two-dimensional (2D) array.

The supporting member 122 may function as a container for retaining an acoustic matching material. In other words, the supporting member 122 may be configured as a container for situating the acoustic matching material between the transducer(s) 121 and the object 100.

The reception unit 120 may include an amplifier for amplifying a time series of analog signals output from the transducer(s) 121. The reception unit 120 may include an analog-to-digital (A/D) converter for converting the time series of analog signals output from the transducer(s) 121 into a time series of digital signals. In other words, the reception unit 120 may include the signal collection unit 140 to be described below.

To detect acoustic signals at various angles, transducers 121 may ideally be arranged to surround the object 100 in all directions. If the transducers 121 are unable to be located to largely surround the object 100 in all directions, the transducers 121 may be arranged on the hemispherical supporting member 122 as illustrated in FIG. 2 to approximate the state of surrounding the object 100 in all directions. While FIG. 2 illustrates only one transducer 121, a plurality of transducers may be arranged on the hemispherical supporting member 122.

The layout and number of transducers 121 and the shape of the supporting member 122 may be optimized according to the object 100. In the present exemplary embodiment, any type of reception unit 120 may be employed.

The space between the reception unit 120 and the object 100 is filled with a medium through which photoacoustic waves can propagate. A material that can transmit acoustic waves, has matching acoustic characteristics at the interfaces with the object 100 and the transducer 121, and has as high transmittance to photoacoustic waves as possible is employed as the medium. Examples of such a medium include water and an ultrasonic gel.

<Driving Unit 130>

The driving unit 130 is a part that changes a relative position between the object 100 and the reception unit 120. In the present exemplary embodiment, the driving unit 130 is a device for moving the supporting member 122 in X and Y directions. The driving unit 130 is a motor-driven XY stage including a stepping motor. The driving unit 130 includes a motor such as a stepping motor for generating driving force, a driving mechanism for transmitting the driving force, and a position sensor for detecting position information about the reception unit 120. Examples of the driving mechanism include a lead screw mechanism, a link mechanism, a gear mechanism, and a hydraulic mechanism. Examples of the position sensor include an encoder, and a potentiometer using a variable resistor.

The driving unit 130 is not limited to one that changes the relative position between the object 100 and the reception unit 120 in the X and Y directions (two-dimensionally). The driving unit 130 may change the relative position one- or three-dimensionally.

The driving unit 130 may fix the reception unit 120 and move the object 100 as long as the relative position between the object 100 and the reception unit 120 can be changed. If the object 100 is moved, the driving unit 130 may be configured to move the object 100 by moving an object supporting unit (not illustrated) that supports the object 100. The driving unit 130 may move both the object 100 and the reception unit 120.

The driving unit 130 may continuously move the relative position. The driving unit 130 may move the relative position in a step-and-repeat manner. The driving unit 130 may be a motor-driven stage or a manual stage.

In the present exemplary embodiment, the driving unit 130 simultaneously drives the light irradiation unit 110 and the reception unit 120 for scanning. However, the driving unit 130 may drive only the light irradiation unit 110 or only the reception unit 120.

<Signal Collection Unit 140>

The signal collection unit 140 includes an amplifier that amplifies the electrical signal which is an analog signal output from the transducer 121, and an A/D converter that converts the analog signal output from the amplifier into a digital signal. The signal collection unit 140 may be configured of a field programmable gate array (FPGA) chip. The digital signal output from the signal collection unit 140 is stored in a storage unit 152 in the computer 150. The signal collection unit 140 is also called a data acquisition system (DAS). As employed herein, an electrical signal is a concept including both analog and digital signals. The signal collection unit 140 may be connected to a light detection sensor attached to the light emission part of the light irradiation unit 110, and may start processing as triggered by and in synchronization with the emission of the pulsed light from the light irradiation unit 110. The signal collection unit 140 may start the processing as triggered by and in synchronization with an instruction given by using a freeze button of an ultrasonographic apparatus.

<Computer 150>

The computer 150 includes an arithmetic unit 151, the storage unit 152, and a control unit 153. Functions of each component will be described along with a description of a processing flow.

The unit in charge of arithmetic functions as the arithmetic unit 151 may include a processor such as a central processing unit (CPU) and a graphics processing unit (GPU), or an arithmetic circuit such as an FPGA chip. Such units may include not only a single processor or arithmetic circuit, but a plurality of processors and arithmetic circuits as well. The arithmetic unit 151 may receive various parameters including an object sound speed and a configuration of a supporting cup from the input unit 170, and process the received signals.

The storage unit 152 may be configured of a non-transitory storage medium such as a read-only memory (ROM), a magnetic disk, and a flash memory. The storage unit 152 may be a volatile memory such as a random access memory (RAM) A storage medium storing a program is a non-transitory storage medium. The storage unit 152 may be configured of not only a single storage medium, but also a plurality of storage media.

The storage unit 152 can store image data representing a photoacoustic image generated by the arithmetic unit 151 with a method to be described below.

The control unit 153 is configured of an arithmetic element such as a CPU. The control unit 153 controls an operation of the components of the photoacoustic apparatus. The control unit 153 may receive instruction signals resulting from various operations such as a start of measurement from the input unit 170 and control the components of the photoacoustic apparatus. The control unit 153 reads program code stored in the storage unit 512 and controls the operation of the components of the photoacoustic apparatus.

The computer 150 may be a workstation designed for dedicated use. The components of the computer 150 may be configured as different pieces of hardware. At least some of the components of the computer 150 may be configured as a single piece of hardware.

Figure 3:
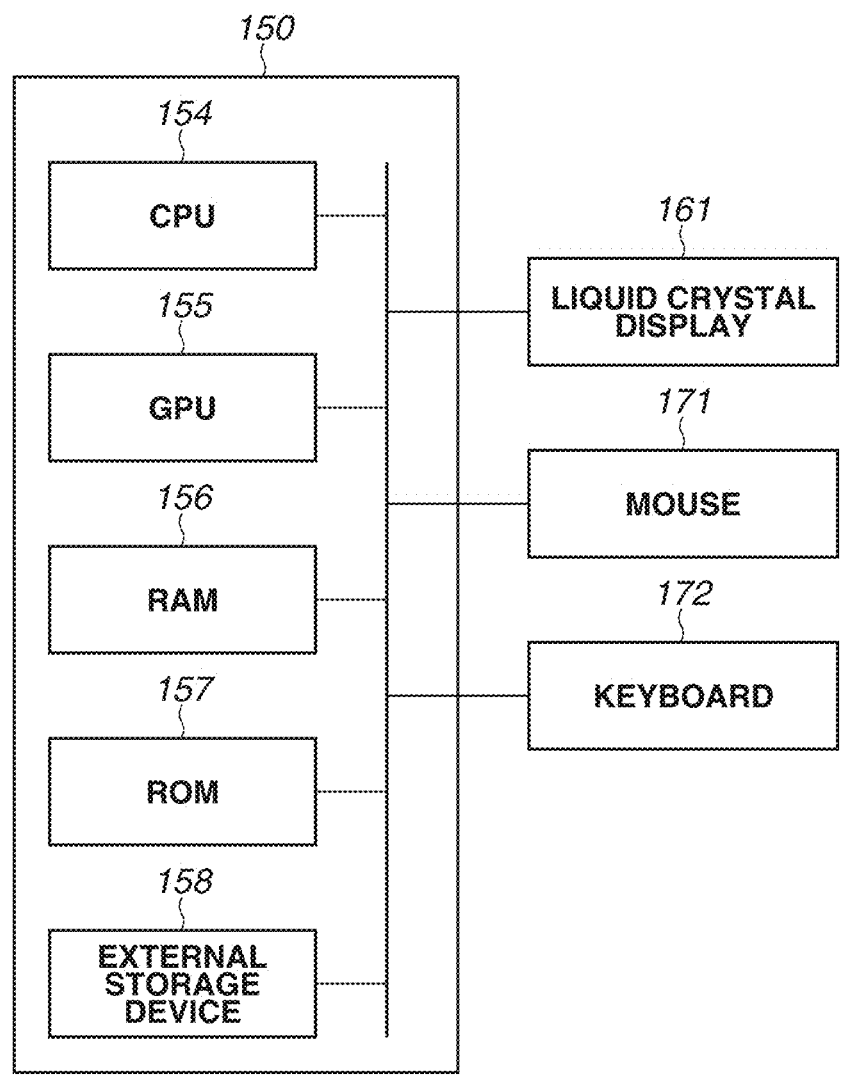
FIG. 3 is a block diagram illustrating a configuration of a computer and its peripheral devices according to the first exemplary embodiment.

FIG. 3 illustrates a specific configuration example of the computer 150 according to the present exemplary embodiment. The computer 150 according to the present exemplary embodiment includes a CPU 154, a GPU 155, a RAM 156, a ROM 157, and an external storage device 158. The computer 150 is connected with a liquid crystal display 161 serving as the display unit 160, and a mouse 171 and a keyboard 172 serving as the input unit 170.

The computer 150 and a plurality of transducers 121 may be configured and provided as accommodated in a common housing. A computer accommodated in the housing may perform part of signal processing while a computer arranged outside the housing performs the rest of the signal processing. In such a case, the computers arranged inside and outside the housing may be collectively referred to as a computer according to the present exemplary embodiment. In other words, the pieces of hardware constituting the computer 150 do not need to be accommodated in one housing.

<Display Unit 160>

The display unit 160 is a display such as a liquid crystal display and an organic electroluminescence (EL) display. The display unit 160 is a device for displaying images based on object information obtained from the computer 150, and numerical values such as a specific position. The display unit 160 may display a GUI for operating images and the photoacoustic apparatus. The display unit 160 or the computer 150 may perform image processing (adjustment of luminance values) before the object information is displayed.

<Input Unit 170>

An operation console including a user-operable mouse and keyboard may be employed as the input unit 170. Contents that can be input from the input unit 170 may include selection of an image reconstruction condition, selection of a method for position shift correction, and selection of an interpolation method. The input unit 170 may be configured so as to allow weights of addition of position shift amounts to be changed by using a slider bar while observing the combined image. The display unit 160 may include a touch panel, in which case the display unit 160 may be used as the input unit 170.

The components of the photoacoustic apparatus may be configured as respective separate devices. Alternatively, the components may be configured as one integrated unit. At least some of the components of the photoacoustic apparatus may be configured as one integrated unit.

<Object 100>

Though being not a component of the photoacoustic apparatus, the object 100 will be described below. The photoacoustic apparatus according to the present exemplary embodiment may be used for purposes such as a diagnosis of a malignant tumor or blood vessel diseases of a person or an animal, and a follow-up of chemotherapy. Therefore, the object 100 may be a living body, or more specifically, a portion to be diagnosed such as the breast, various organs, a blood vessel network, the head, the neck, the abdomen, and extremities including hand fingers and toes of a human body or an animal. For example, if the measurement target is a human body, oxyhemoglobin, deoxyhemoglobin, blood vessels containing high proportion thereof, or newborn blood vessels formed near a tumor may be assumed as a target light absorber. Plaque on a carotid wall may be assumed as a target light absorber. Dyes such as methylene blue (MB) and indocyanine green (ICG), fine gold particles, and externally-introduced substances obtained by aggregating or chemically modifying the same may be used as a target light absorber.

Figure 4:
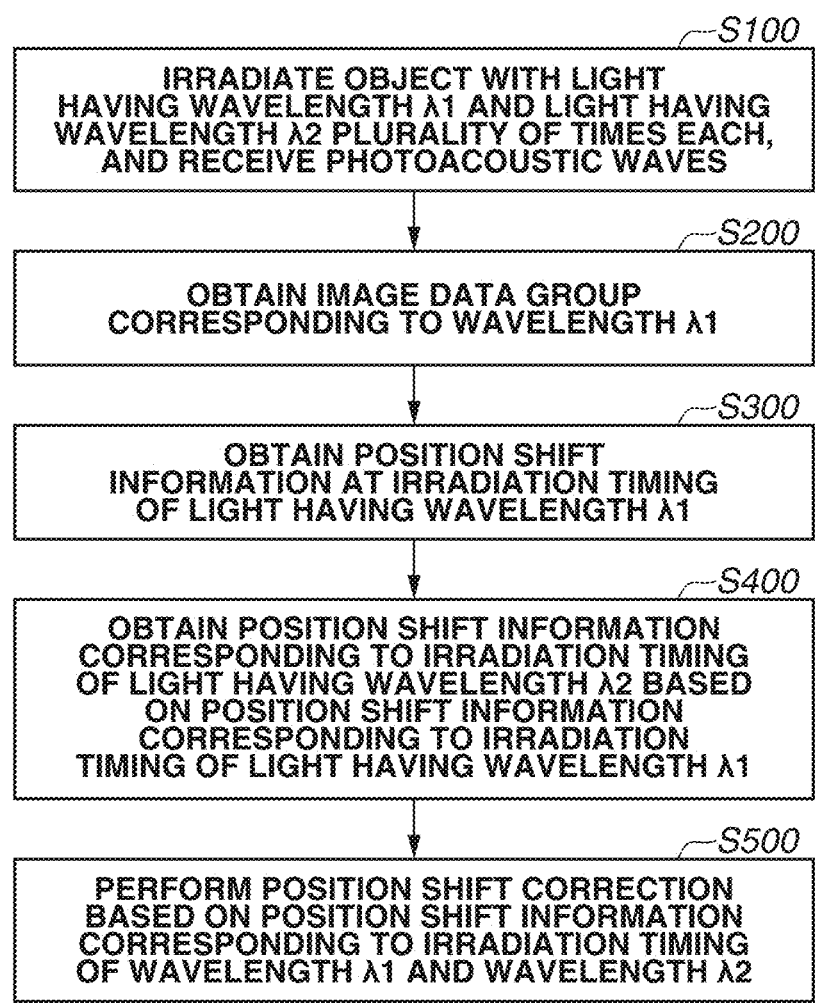
FIG. 4 is a flowchart illustrating an operation of the photoacoustic apparatus according to the first exemplary embodiment.

An operation of the photoacoustic apparatus, including information processing according to the present exemplary embodiment, will be described below with reference to a flowchart illustrated in FIG. 4.

<Step S100: Step of Irradiating Object with Light Having Wavelength λ1 and Light Having Wavelength λ2 Plurality of Times Each and Receiving Photoacoustic Waves>

In step S100, the light irradiation unit 110 irradiates the object 100 with light having mutually different wavelengths λ1 and λ2 a plurality of times each. The reception unit 120 receives photoacoustic waves generated by the light irradiation.

The control unit 153 transmits scanning information and information (control signal) indicating light irradiation to the probe 180. While the driving unit 130 moves the reception unit 120, the light irradiation unit 110 irradiates the object 100 with the pulsed light of the plurality of wavelengths a plurality of times. In other words, the driving unit 130 moves the reception unit 120 during a period in which light irradiation is performed a plurality of times. As a result, the driving unit 130 can move the reception unit 120 so as to locate the reception unit 120 at different positions at respective times of light irradiation. The transducer 121 receives the photoacoustic waves generated by the plurality of times of light irradiation with the pulsed light by the light irradiation unit 110, and outputs signals as many as the number of times of light irradiation. The signals output as many as the number of times of light irradiation with the plurality of wavelengths will be collectively referred to as a signal group corresponding to the plurality of wavelengths.

A case in which the light irradiation is performed N times will be described below. A signal obtained by the ith light irradiation with the wavelength λ1 will be denoted as:

$$S_{\lambda 1, i} (1 \leq i \leq N).$$

An item with a subscript i represents one corresponding to the ith light irradiation. i is a positive integer and may be referred to as a pulse index.

Figure 5:
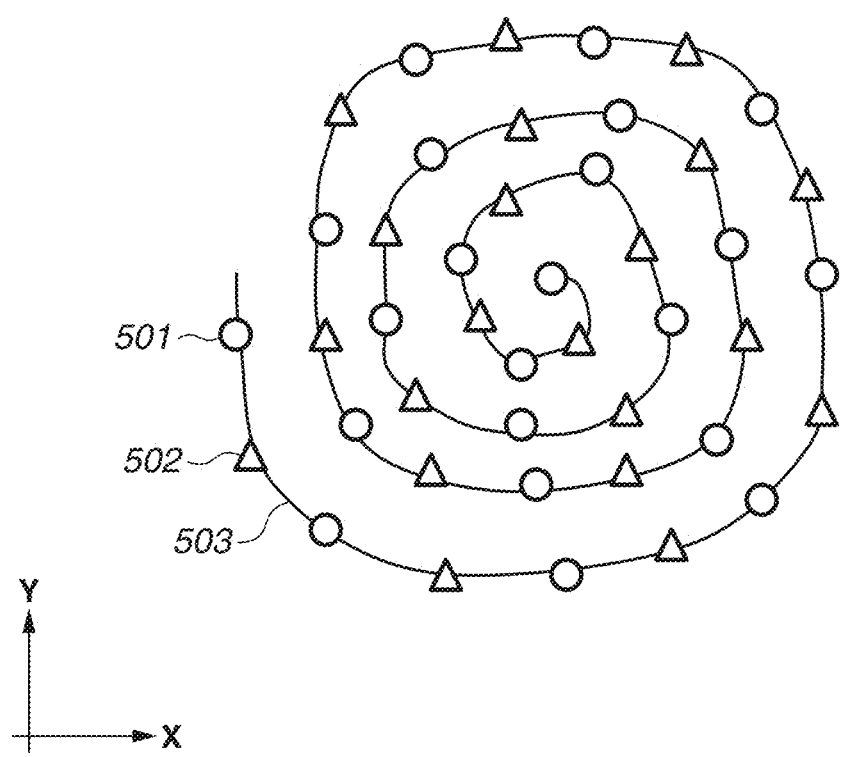
FIG. 5 is a diagram illustrating measurement positions of the photoacoustic apparatus according to the first exemplary embodiment.

For example, the light irradiation and the reception of the photoacoustic waves can be performed while the probe 180 is moved as illustrated in FIG. 5. Circles 501 represent positions (measurement positions) of the probe 180 when the object 100 is irradiated with the light having the wavelength λ1. Triangles 502 represent positions (measurement positions) of the probe 180 when the object 100 is irradiated with the light having the wavelength λ2. A solid line 503 indicates the track of the probe 180. As illustrated in FIG. 5, in the present exemplary embodiment, the driving unit 130 may move the probe 180 while the light irradiation unit 110 alternately irradiates the object 100 with the light of the plurality of wavelengths. In the example illustrated in FIG. 5, the probe 180 is scanned in a spiral pattern inward from the outermost periphery of the track. For the sake of convenience, FIG. 5 illustrates the track on the XY plane. However, the probe 180 may be scanned three-dimensionally, not necessarily on a plane.

The signal collection unit 140 performs A/D conversion processing on the signal groups corresponding to the plurality of wavelengths, which is an analog signal groups output from the transducer 121, and transmits the processed photoacoustic signals to the computer 150. The photoacoustic signals as digital signal groups are stored in the storage unit 152.

<Step S200: Step of Obtaining Image Data Group Corresponding to Wavelength λ1>

In step S200, the arithmetic unit 151 obtains an image data group corresponding to the light irradiation at the first wavelength (wavelength λ1) based on the signal group obtained in step S100. The arithmetic unit 151 may generate pieces of image data from the respective signals of light irradiation, and obtain image data resulting from the light irradiation with the wavelength λ1 from the pieces of image data. The arithmetic unit 151 may obtain the image data resulting from the light irradiation with the wavelength λ1 by selectively using signals corresponding to the light irradiation at the wavelength λ1 in the signal group.

The arithmetic unit 151 generates a photoacoustic image by performing reconstruction processing such as universal back-projection (UBP) on the photoacoustic signals. After the generation of the photoacoustic image, the photoacoustic signals stored in the storage unit 152 may be deleted. Image data obtained by irradiation with the pulsed light of one time may be referred to as pulse volume data. The pulse volume data is obtained in the form of volume data in which voxels arranged two- or three-dimensionally (in a case of a 2D arrangement, may be referred to as pixels) store values in respective positions. The volume data may be referred to as a two- or three-dimensional volume, a two- or three-dimensional image, and a two- or three-dimensional tomographic image.

Conventional reconstruction techniques such as a time domain reconstruction technique, a Fourier domain reconstruction technique, and a model base reconstruction technique (repetitive reconstruction technique) may be employed. For example, a time domain reconstruction technique called UBP, discussed in Physical Review E71, 016706 (2005), may be employed.

For the image data, the arithmetic unit 151 may obtain initial sound pressure distribution data:

$$P_{\lambda a, i} (1 \leq a \leq L, 1 \leq i \leq N).$$

Here, a is a wavelength index indicating that the item corresponds to light irradiation with a wavelength λa. The arithmetic unit 151 may obtain the initial sound pressure distribution data based on position information about the transducer 121 during light irradiation, in addition to the signal group. The arithmetic unit 151 can obtain the position information by reading the position information about the transducer 121 at each time of light irradiation, stored in advance in the storage unit 152. The arithmetic unit 151 may obtain the position information about the transducer 121 by receiving position information about the reception unit 121 from the position sensor included in the driving unit 130, with light irradiation as a trigger.

Figure 6:
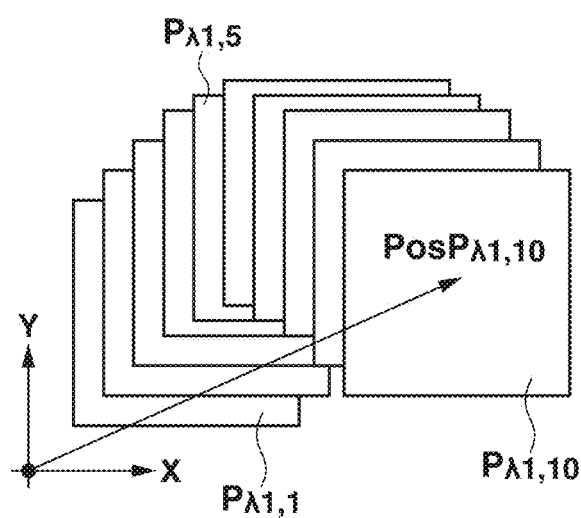
FIG. 6 is a diagram illustrating pulse volume data according to the first exemplary embodiment.

FIG. 6 illustrates a part ($P_{\lambda 1,1}$ to $P_{\lambda 1,10}$) of the pulse volume data with the wavelength λ1 according to the present exemplary embodiment. The pulse volume data according to the present exemplary embodiment is volume data in a three-dimensional space, whereas the pulse volume data is expressed on the XY plane for the convenience of illustration. In the present exemplary embodiment, a reconstruction area is set so that at least some of the areas of temporally adjoining pieces of initial sound pressure distribution data overlap. In the present exemplary embodiment, a 60-mm-side cubic area around the center of curvature of the hemispherical supporting member 122 is set as a reconstruction area to be reconstructed based on one round of light irradiation, i.e., one electrical signal group. The size (60 mm) of the reconstruction area for one round of light irradiation is greater than the amount of movement of the reception unit 120 during the light irradiation. Therefore, as illustrated in FIG. 6, two or more pieces of pulse volume data corresponding to a temporal series of light irradiation overlap. The size and shape of the reconstruction area may be set in advance. The user may specify the size and shape of the reconstruction area by using the input unit 170. The center position of each piece of pulse volume data with respect to a reference position will be referred to as the position of the piece of pulse volume data. For example, FIG. 6 illustrates a position $PosP_{\lambda 1,10}$ of the pulse volume data $P_{\lambda 1,10}$. In this example, the position of the reception unit 120 changes at each round of light irradiation. The pieces of pulse volume data obtained in the present exemplary embodiment, illustrated in FIG. 6, are thus located in respective different positions with respect to the reference position.

In the present step, the arithmetic unit 151 may obtain light fluence distribution data Φ [Pa·m$^3$/J] inside the object 100. The arithmetic unit 151 may divide the initial sound pressure data by the light fluence distribution data Φ and Grüneisen parameter distribution data to obtain light absorption coefficient distribution data μa [1/m] inside the object 100. In such a case, the light absorption coefficient distribution data μa may be used as pulse volume data.

For example, as discussed in Proc. of SPIE, Vol. 7561, 756117-1, the arithmetic unit 151 may solve an optical diffusion equation to obtain the light fluence distribution data Φ.

For example, the value of the Grüneisen parameter is known to be almost uniquely determined once the type of the object 100 is determined. Grüneisen parameter distribution data Γ corresponding to the object 100 may therefore be stored in the storage unit 152 in advance. The arithmetic unit 151 may read and obtain the Grüneisen parameter distribution data Γ stored in the storage unit 152 in advance.

The user may hold a probe 180 having a grip portion and move the probe 180. The probe 180 may be maintained stationary during a period in which light irradiation is performed a plurality of times. The arithmetic unit 151 may obtain image data on the entire imaging area based on the electrical signal group obtained by one round of light irradiation, and repeat the process for a plurality of rounds of light irradiation.

<Step S300: Step of Obtaining Position Shift Information Corresponding to Irradiation Timing of Light Having Wavelength λ1>

In step S300, the arithmetic unit 151 obtains position shift information corresponding to the irradiation timing of the light having the wavelength λ1 based on the image data group corresponding to the wavelength λ1, obtained in step S200. For example, as will be described below, the arithmetic unit 151 can obtain the position shift information by calculating a position shift amount between pieces of pulse volume data or by calculating a position shift amount of volume data obtained by combining pieces of pulse volume data.

First, the arithmetic unit 151 estimates the position shift amounts of the respective pieces of pulse volume data due to variations in the relative positional relationship between the object and the reception unit 120, between the rounds of light irradiation with the wavelength λ1. At that time, the arithmetic unit 151 selects an arbitrary pair of pieces of pulse volume data from the obtained pulse volume data. A kth pair will be denoted as R_k. Either one of the pieces of pulse volume data of the wavelength λ1, constituting the pair R_k, will be denoted as $P_{\lambda1,k1}$. The other will be denoted as $P_{\lambda1,k2}$. In the present exemplary embodiment, a case in which K pairs are selected will be described below. Two pieces of pulse volume data having an overlapping area may be desirably selected as a pair. This can avoid comparing pieces of pulse volume data having no feature in common, and can thus reduce redundant calculations. Further, pieces of pulse volume data having a large overlapping area may desirably be selected as a pair. Therefore, for example, the arithmetic unit 151 may select a pair of pieces of pulse volume data between which the volume ratio of an overlapping area is greater than or equal to a predetermined value. If, as will be described below, combined volume data is used for position shift correction, pieces of pulse volume data each overlapping with a large number of pieces of pulse volume data may be selected as a pair.

A piece of pulse volume data and another piece of volume data having an index falling within a predetermined range with respect to the index of the piece of pulse volume data may be selected to be paired. Pieces of pulse volume data having consecutive indexes, i.e., temporally continuous pieces of pulse volume data may be selected to be paired. For example, in the present exemplary embodiment, the arithmetic unit 151 selects pieces of pulse volume data having an overlapping area greater than or equal to 50% as a pair.

An example of a method for estimating the position shift amount of each piece of pulse volume data will be described below.

The arithmetic unit 151 calculates a similarity function F_k between $P_{\lambda1,k1}$ and $P_{\lambda1,k2}$ as expressed by Eq. 1:

$$F\_k(x,y,z)=f_{simil}(P\_k,x,y,z). \quad \text{Eq. 1}$$

The similarity function F_k is a function for calculating similarity when, with respect to one of the pieces of pulse volume data constituting the pair R_k, or $P_{\lambda1,k1}$, the relative position of the other piece of pulse volume data $P_{\lambda1,k2}$ is translated by (x, y, z). The function $f_{simil}$ returns a high value as a function value if the similarity between the images is high. Obtaining a similarity function F refers to obtaining its function values when the arguments of the function or the amount of translation (x, y, z), or equivalently, the relative position between the pieces of image data is discretely changed within a predetermined range. For example, suppose that the values of x, y, and z are each changed as integer values in the range of −L to +L. In such a case, obtaining the similarity function F refers to obtaining a set of (2L+1)×(2L+1)×(2L+1) values that the similarity function F returns in the respective cases. As an advanced approach, the similarity function F may be derived and obtained in the form of information closer to a continuous function by applying a bilinear method or bicubic method to the set of (2L+1)×(2L+1)×(2L+1) values.

The arithmetic unit 151 may obtain function values when the position of $P_{\lambda1,k2}$ is discretely changed within a predetermined range with reference to a position to which $P_{\lambda1,k2}$ is translated by the relative position of $P_{\lambda1,k2}$ to $P_{\lambda1,k1}$ (the moving amount of the reception unit 120 between the two rounds of light irradiation).

For example, an arbitrary similarity scale such as the sum of squared differences (SSD), the sum of absolute differences (SAD), a mutual information amount, and cross correlation may be applied as the function for calculating the similarity. For example, feature shapes may be extracted from the pulse volume data, and the degree of coincidence with the positions of such shapes may be measured to obtain a similarity function. Features to be extracted may include anatomical features of blood vessels and features extracted by conventional methods commonly used in the field of image processing, such as edge detection and corner detection. Features to be extracted may include local image features of higher order commonly used in the technical field of computer vision, such as scale-invariant feature transform (SIFT) features and speeded up robust features (SURF). According to such methods, a more robust similarity function can be obtained depending on a difference in luminance distribution between the pieces of pulse volume data and inclusion of noise.

The arithmetic unit 151 may obtain a similarity function by applying processing for multiplying the result of calculation of similarity by a weight.

If similarity fails to be correctly calculated between the pieces of pulse volume data to be a target of the similarity calculation, the result does not need to be used for subsequent processing. Situations in which the similarity can fail to be correctly calculated include when the similarity remains sufficiently small or unchanged even if the pieces of pulse volume data are translated in any direction. According to such processing, the result of comparison (similarity function) between pieces of pulse volume data in which the same features appear sufficiently can be selectively used for subsequent processing.

The arithmetic unit 151 then obtains a translation amount M_k that maximizes the function value of the similarity function F_k as expressed by Eq. 2:

$$M\_k = \arg\max(F\_k(x,y,z)). \quad \text{Eq. 2}$$

The arithmetic unit 151 obtains the translation amount M_k that maximizes the function value of the similarity function F_k for each pair.

An evaluation function will be defined to maintain the translation amount M_k, which is an individual optimum value for a pair R_k, as much as possible in estimating the positions of the pieces of pulse volume data. More specifically, the evaluation function is defined so that its value decreases as the position of $P_{\lambda1,k2}$ with respect to $P_{\lambda1,k1}$ deviates from the translation amount M_k. An example of such an evaluation function E_k is expressed by Eq. 3:

$$E\_k = (M\_k - (\mathrm{Pos}P_{\lambda1,k1} - \mathrm{Pos}P_{\lambda1,k2})^2) = (M\_k(x) - (\mathrm{Pos}P_{\lambda1,k1(x)} - \mathrm{Pos}P_{\lambda1,k2(x)})^2) + (M\_k(y) - (\mathrm{Pos}P_{\lambda1,k1(y)} - \mathrm{Pos}P_{\lambda1,k2(y)})^2) + (M\_k(z) - (\mathrm{Pos}P_{\lambda1,k1(z)} - \mathrm{Pos}P_{\lambda1,k2(z)})^2). \quad \text{Eq. 3}$$

$\mathrm{Pos}P_{\lambda1,k1}$ represents the position of $P_{\lambda1,k1}$ with respect to a reference position. $\mathrm{Pos}P_{\lambda1,k2}$ represents the position of $P_{\lambda1,k2}$ with respect to the reference position. In defining the evaluation function, the similarity function F_k may be approximated by a quadratic function that fits to the similarity function F_k. If the similarity function F_k can be approximated to decrease according to a quadratic function in the vicinity of the translation amount M_k, Eq. 3 serves as a function for approximating the value of the similarity function F_k in the vicinity of the translation amount M_k based on the positional relationship of $P_{\lambda1,k1}$ and $P_{\lambda1,k2}$.

The arithmetic unit 151 then obtains positions PosP'$_{\lambda 1,j}$ of all the pieces of pulse volume data with respect to the reference position when a cost function E defined by Eq. 4 is minimized. Here, j is a pulse index for a specific pulse.

$$E = \sum_{k=1}^{K} E\_k$$

$$= \sum_{k=1}^{K} (M\_k - (PosP_{\lambda 1,k1} - PosP_{\lambda 1,k2})^2)$$

$$= \sum_{k=1}^{K} \{(M\_k(x) - (PosP_{\lambda 1,k1(x)} - PosP_{\lambda 1,k2(x)})^2) +$$

$$(M\_k(y) - (PosP_{\lambda 1,k1(y)} - PosP_{\lambda 1,k2(y)})^2) +$$

$$(M\_k(z) - (PosP_{\lambda 1,k1(z)} - PosP_{\lambda 1,k2(z)})^2)\}$$

Eq. 4

The position of a piece of pulse volume data with respect to the reference position when the cost function E is minimized indicates the position information about the piece of pulse volume data after a position shift due to a change in the relative positional relationship between the object 100 and the reception unit 120.

For example, the arithmetic unit 151 obtains a solution that minimizes (brings closest to 0) the cost function E expressed in Eq. 4, by using a linear least-squares method. In such a manner, the position PosP'$_{\lambda 1,j}$ of each piece of pulse volume data can be uniquely obtained with a low calculation cost.

The cost function E may be optimized by using any conventional method, not necessarily by the linear optimization described above. For example, the cost function E may be optimized by a nonlinear optimization method using repetitive calculations, such as a steepest descent method and a Newton method. More specifically, the arithmetic unit 151 searches for the positions of the pieces of pulse volume data that minimize the cost function E, and thereby obtains the position information about the pulse volume data with respect to the reference position after a position shift.

The cost function E may be defined to regularize possible variations (motions) of the positions of the pieces of pulse volume data between the rounds of light irradiation. If the object 100 is the breast, respiratory motions are considered to be dominant. In such a case, the motion of the object 100 is approximately several millimeters at maximum, and the motion is expected to be temporally continuous and smooth. The motion is also expected to be periodic. Regularization can thus be performed so as to suppress calculation of motions deviating from such an expected motion of the object 100.

The regularization may be performed by any method. For example, a predetermined weighting factor may be applied to the total sum of the amounts of variations (moving distances) of the object 100 in the process of derivation, and the resultant may be added to the cost function E for regularization. A value calculated based on a frequency component value of variations of the object 100 may be added to the cost function E. A model of typical variation behavior of the object 100 may be prepared, and differences from the variations of the model may be added as a cost to the cost function E.

That "the cost function E is minimized" includes not only a case in which the cost function E is minimized in a strict sense, but also a case in which the value of the cost function E falls to or below a predetermined value and a case in which the amount of change of the cost function E falls to or below a predetermined value when a candidate solution is changed. In other words, the arithmetic unit 151 may determine that the cost function E is minimized if the cost function E satisfies a predetermined condition. The user may give an instruction that the cost function E is minimized, by using the input unit 170. In such a case, the arithmetic unit 151 receives the instruction from the input unit 170 and determines that the cost function E is minimized.

The arithmetic unit 151 then obtains a position shift amount Mopt$_{\lambda 1,j}$ of each piece of pulse volume data when the cost function E is minimized. The position shift amount Mopt$_{\lambda 1,j}$ indicates the position shift amount of each piece of pulse volume data due to a variation in the relative positional relationship between the object 100 and the reception unit 120.

Figure 7:
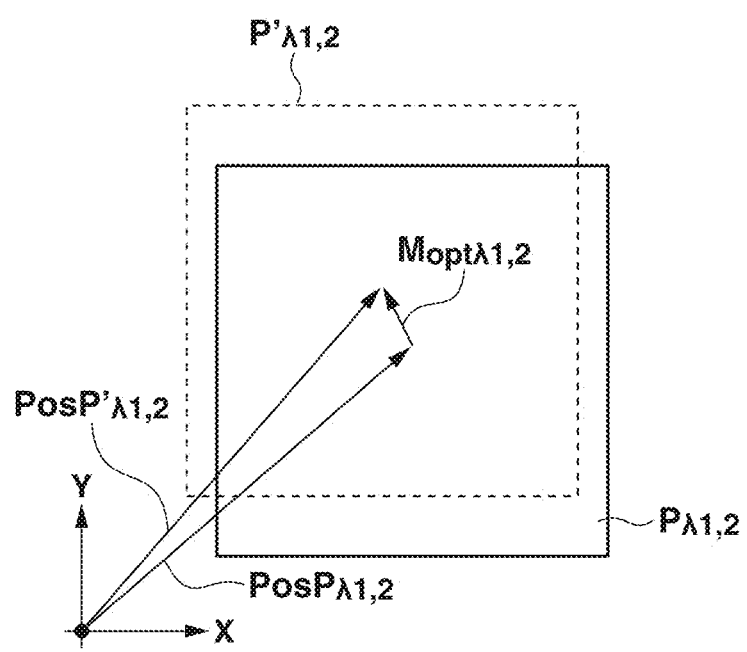
FIG. 7 is a diagram illustrating a position shift amount between images according to the first exemplary embodiment.

FIG. 7 illustrates the position PosP$_{\lambda 1,2}$ of the pulse volume data P$_{\lambda 1,2}$ and the position PosP'$_{\lambda 1,2}$ of pulse volume data P'$_{\lambda 1,2}$ when the cost function E is minimized by the foregoing method. In FIG. 7, the pulse volume data P$_{\lambda 1,2}$ is illustrated in solid lines, and the pulse volume data P'$_{\lambda 1,2}$ when the cost function E is minimized is illustrated in broken lines.

In the present step, any method may be used as long as the position shift information about the pulse volume data due to a variation in the relative position between the object 100 and the reception unit 120 can be obtained.

The arithmetic unit 151 may obtain the position shift information by using a kth piece of combined volume data G$_{\lambda 1,k}$ of the wavelength λ1, obtained by combining two or more pieces of pulse volume data. In such a case, a minimum rectangular area that includes all the pieces of pulse volume data combined may be used as the combined volume data. An arbitrary area including an area in which at least two pieces of pulse volume data overlap may be used as the combined volume data. In other words, the area of the combined volume data does not need to include all the pulse volume data to be combined.

The combined volume data is obtained by adding the selected pieces of pulse volume data according to their respective positions. Alternatively, the selected pieces of pulse volume data may be added and divided by the number of overlapping pieces of pulse volume data to determine average volume data. Any technique may be used as long as volume data that reproduces the features of the object 100 more precisely can be obtained. As employed herein, the "combination" does not include processing for correcting a variation in the relative position of the object 100 and the reception unit 120 between the rounds of light irradiation (e.g., processing for changing the position of pulse volume data).

For example, the arithmetic unit 151 may assign weights to the respective pieces of pulse volume data to be combined, and then add the resultant for combination. The arithmetic unit 151 may calculate an added value or an average value of pulse volume data from which values including much noise are excluded by an outlier removal method.

By such combination processing, combined volume data in which noise included in each piece of pulse volume data is reduced and which more precisely reproduces the features of the object 100 can be obtained. If the number of pieces of combined volume data is smaller than the number of pieces of pulse volume data, the amount of calculation and the calculation cost can be reduced, compared to a technique in which the pieces of pulse volume data are compared to estimate a position shift of the entire pulse volume data.

Note that the combined volume data obtained by such combination is affected by variations in the relative positional relationship of the object 100 and the reception unit 120 of photoacoustic waves between the plurality of times of light irradiation. Thus, the combined volume data can include a drop in quality due to such variations. Processing for estimating the position of pulse volume data from the estimated position of combined volume data to suppress such a drop in quality will be described below.

The arithmetic unit 151 estimates the position shift amount $Mopt_{\lambda 1,j}$ of each piece of pulse volume data based on a position shift amount $MGopt_{\lambda 1,j}$ of each piece of combined volume data at the wavelength $\lambda 1$.

The arithmetic unit 151 can assign the estimated position shift amounts of the combined volume data to those of pieces of pulse volume data associated with the combined volume data. The arithmetic unit 151 can estimate the position shift amounts of the other pieces of pulse volume data by performing interpolation processing on the assigned position shift amounts of the pulse volume data. Conventional techniques such as linear interpolation and spline interpolation can be used for the interpolation processing. The interpolation processing may be performed under a constraint so as not to calculate positions deviating from the expected motion of the object 100.

An arbitrary piece of pulse volume data among the pieces of pulse volume data to be combined may be used as the pulse volume data associated with the combined volume data. For example, if there are an odd number of pieces of pulse volume data to be combined, the piece of pulse volume data lying temporally in the center may be associated with the combined volume data.

For example, if there are an even number of pieces of pulse volume data to be combined as in the present exemplary embodiment, either one of the pieces of pulse volume data lying temporally near the center may be associated with the combined volume data. For example, if there are ten pieces of pulse volume data to be combined as in the present exemplary embodiment, the position shift amount $MGopt_{\lambda 1,j}$ of the combined volume data $G_{\lambda 1,j}$ at the wavelength $\lambda 1$ may be assigned to the position shift amount $Mopt_{\lambda 1,5}$ of the pulse volume data $P_{\lambda 1,5}$.

If there are an even number of pieces of pulse volume data to be combined, a virtual piece of pulse volume data lying temporally in the center may be associated with the combined volume data. For example, if there are 10 pieces of pulse volume data to be combined as in the present exemplary embodiment, the position shift amount $MGopt_{\lambda 1,j}$ of the combined volume data $G_{\lambda 1,j}$ at the wavelength $\lambda 1$ may be assigned to the position shift amount of virtual pulse volume data with a pulse index of 5.5j.

In the case of weighted combination, a piece of pulse volume data to which the highest weighting factor is assigned among the pieces of pulse volume data to be combined may be associated with the combined volume data. A piece of pulse volume data having a median weighting factor among the pieces of pulse volume data to be combined may be associated with the combined volume data.

By the foregoing processing, the position shift information about the pulse volume data corresponding to the wavelength $\lambda 1$ can be obtained based on the position shift information about the combined volume data corresponding to the wavelength $\lambda 1$. In such a manner, the position shift information corresponding to the irradiation timing of the light having the wavelength $\lambda 1$ may be obtained.

The position shift information may be obtained in a manner similar to the foregoing manner by using 2D projection data such as maximum intensity projection (MIP) of the pulse volume data or the combined volume data. An example of such processing will be described below.

The arithmetic unit 151 obtains MIP data of the combined initial sound pressure distribution data $G_{\lambda 1,j}$ at the wavelength $\lambda 1$ as projection data projected in each of the X, Y, and Z directions. The MIP data projected in the X direction is 2D spatial distribution information indicated by the Y- and Z-axes, and is denoted as $IG_{\lambda 1,j}(y, z)$. The MIP data projected in the Y direction is 2D spatial distribution information indicated by the Z- and X-axes, and is denoted as $IG_{\lambda 1,j}(z, x)$. The MIP data projected in the Z direction is 2D spatial distribution information indicated by the X- and Y-axes, and is denoted as $IG_{\lambda 1,j}(x, y)$.

Projection techniques other than MIP images may be employed as long as three-dimensional image data can be converted into 2D image data. For example, minimum intensity projection (MINP) images may be generated and used instead of MIP images. A plurality of slides in a projection direction may be added to obtain projection data.

On each of the XY, YZ, and ZX planes, the arithmetic unit 151 translates the relative position of the other piece of MIP data to be paired with one piece of MIP data, and calculates similarity. The similarity can be calculated by using the technique described above. Then, the arithmetic unit 151 calculates translation amounts MX_k, MY_k, and MZ_k that maximize the similarity of $P_{\lambda 1,k2}$ with respect to $P_{\lambda 1,k1}$ on the XY, YZ, and ZX planes, and calculates average values of the respective coordinate-axis components of the translation amounts as component values of a three-dimensional translation amount M that maximizes the similarity.

$$M\_k = \left(\frac{MY\_k + MZ\_k}{2}, \frac{MX\_k + MZ\_k}{2}, \frac{MX\_k + MY\_k}{2}\right) \quad \text{Eq. 5}$$

Next, by using the translation amount M_k expressed by Eq. 5, the arithmetic unit 151 can estimate the position of each piece of combined volume data when the cost function E expressed by Eq. 4 is minimized.

By the foregoing processing, the position of the combined volume data with respect to the reference position can be obtained based on the 2D image data converted from the three-dimensional image data. The conversion from three-dimensional image data into 2D image data allows the acquisition of the position of the position-shifted volume data with less calculation cost, compared to when the three-dimensional image data is simply processed.

The position shift information about the pulse volume data corresponding to the wavelength $\lambda 1$ may be obtained by the foregoing method by converting three-dimensional image data (pulse volume data) into 2D image data. The position shift information corresponding to the irradiation timing of the light having the wavelength $\lambda 1$ can be obtained in such a manner.

An example of a case in which translation occurs as a variation in the relative positional relationship between the object 100 and the reception unit 120 has so far been described. If a rotation or deformation occurs as the variation, the resulting position shift amount can also be estimated in a similar manner.

For example, if a rotation is taken into consideration, the arithmetic unit 151 can estimate a position and a rotation amount (position shift amount) of each piece of pulse volume data by using a rotation amount as an argument in addition to a translation amount. The arithmetic unit 151 can then perform rigid body conversion processing (position shift correction processing) on the pieces of pulse volume data based on the estimated positions and rotation amounts, and combine the resultant to obtain combined volume data. Only the rotation amount may be used as the position shift amount. Alternatively, a calculated conversion matrix such as a two- or three-dimensional translation and rotation matrix, and various parameters for conversion may be used as position shift amounts.

For example, if a deformation is taken into consideration, the arithmetic unit 151 can estimate a displacement amount by using a displacement amount (at least either one of translation and rotation amounts) at each point set on the pulse volume data as an argument. The arithmetic unit 151 can then perform deformation processing (position shift correction processing) on the pieces of pulse volume data based on the estimated displacement amounts, and combine the resultant to obtain combined volume data. For example, a displacement amount between pieces of pulse volume data can be calculated by using a deformation-expressing technique such as free form deformation (FFD) and thin plate splines. By such processing, high-order variations including a deformation can be taken into consideration to obtain combined volume data of high quality.

In the present exemplary embodiment, the acquisition of the pulse volume data is described to be started after the completion of the measurement of the photoacoustic waves resulting from the entire light irradiation. However, the pieces of pulse volume data may be obtained each time light irradiation is performed. In the latter case, the obtained pieces of pulse volume data may be successively displayed on the display unit 160. This allows the user to check the obtained pulse volume data before the completion of the entire measurement. In this case, areas in which the pieces of pulse volume data overlap may be combined by the foregoing method.

In the present exemplary embodiment, the position shift amounts are calculated after the acquisition of the entire pulse volume data. However, position shift amounts may be successively calculated by using obtained pulse volume data upon each time light irradiation is performed. A specific number of pieces of pulse volume data among the successively-obtained pieces of pulse volume data may be combined to generate combined volume data, and position shift amounts may be successively calculated.

The volume data for calculating a position shift amount may be subjected to preprocessing such as removal of negative values and normalization of image intensity before use.

<Step S400: Step of Obtaining Position Shift Information Corresponding to Irradiation Timing of Light Having Wavelength λ2 Based on Position Shift Information Corresponding to Irradiation Timing of Light Having Wavelength λ1>

In step S400, the arithmetic unit 151 obtains position shift information corresponding to the irradiation timing of the light having the wavelength λ2 based on the position shift information corresponding to the irradiation timing of the light having the wavelength λ1, obtained in step S300. In other words, the arithmetic unit 151 calculates position shift information corresponding to another wavelength from position shift information corresponding to a specific wavelength, calculated by the method described in step S300. For example, if the irradiation timing of the light is known, the arithmetic unit 151 may temporally interpolate the position shift information corresponding to the irradiating timing of the light having the wavelength λ1. If the position of the probe 180, i.e., the position of the reception unit 120 corresponding to the irradiation timing of the light is known, the arithmetic unit 151 may spatially interpolate the position shift information corresponding to the irradiation timing of the light having the wavelength λ1. The arithmetic unit 151 may obtain the position shift information corresponding to the irradiation timing of the light having the wavelength λ2 by such interpolation.

Figure 8:
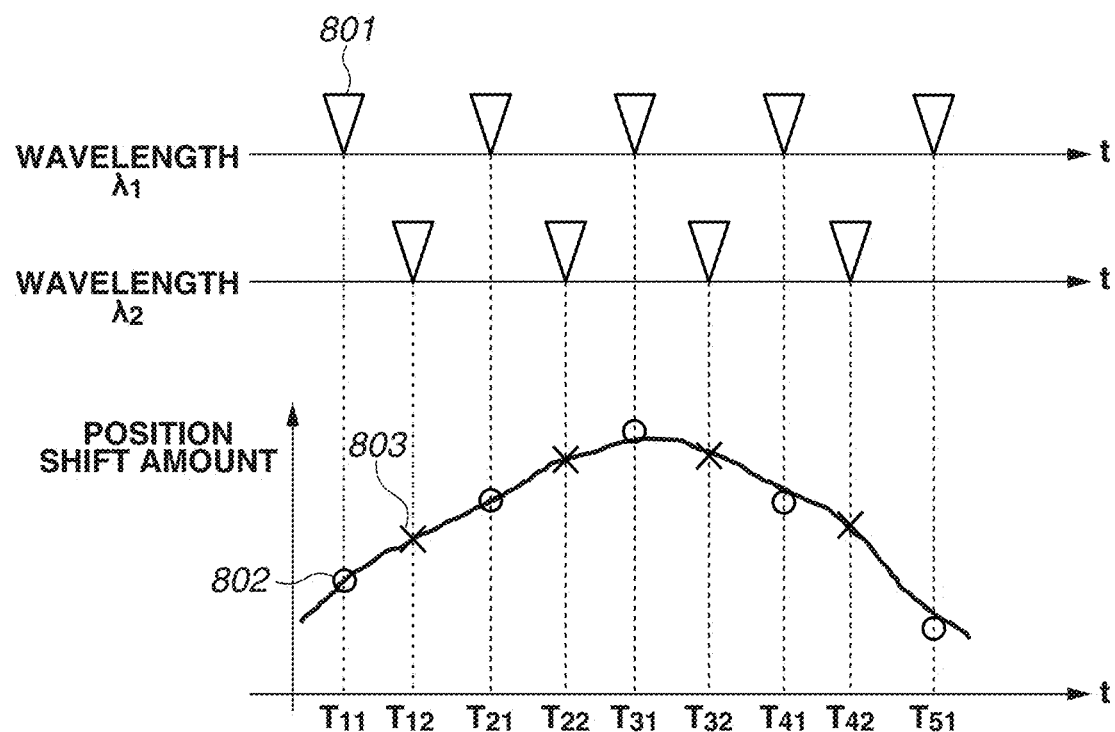
FIG. 8 is a sequence diagram illustrating temporal interpolation of position shift amounts according to the first exemplary embodiment.

A case in which the position shift information is calculated by temporal interpolation will be described with reference to FIG. 8. FIG. 8 includes a sequence diagram illustrating the irradiation timing of pulsed light having a plurality of wavelengths over time t. FIG. 8 includes a graph illustrating position shift amounts (translation amounts) corresponding to respective pulses of light having the wavelength λ1. Inverse triangles 801 schematically represent the irradiation timings of the pulsed light. It can be seen that the pulsed light having the wavelength λ1 is emitted at times T11, T21, T31, T41, and T51. It can also be seen that the pulsed light having the wavelength λ2 is emitted at times T12, T22, T32, T42, and T52. The position shift amounts corresponding to the irradiation timing of the pulsed light having the wavelength λ1 are calculated in step S300. In FIG. 8, the position shift amounts are plotted with circle marks 802. The arithmetic unit 151 then calculates the position shift amounts corresponding to the wavelength λ2 by temporally interpolating the position shift amounts of the wavelength λ1. In FIG. 8, X marks 803 represent the position shift amounts corresponding to the irradiation timings of the pulsed light having the wavelength λ2, calculated by temporal interpolation. Lanczos interpolation is ideally used as the method of interpolation, whereas any other interpolation methods may be used, including linear interpolation, cubic interpolation, and spline interpolation. Here, examples in which linear interpolation and Lanczos interpolation are used will be described. For example, if the motion of the object 100 under observation is slower than the pulse irradiation time (sampling time) of the wavelength λ1, the position shift amount corresponding to the timing T12 of the wavelength λ2 can be calculated from the position shift amounts at the times T11 and T21 corresponding to the wavelength λ1. A position shift amount M12 at the time T12 may be calculated by the following Eq. 6:

$$M12 = \frac{M11 \cdot (T21 - T12) + M21 \cdot (T12 - T11)}{T21 - T11}, \quad \text{Eq. 6}$$

where M11 and M21 are the position shift amounts at times T11 and T21, respectively.

Here, the position shift amount M12 of the pulse of the wavelength λ2 at time T12 is calculated by using the position shift amounts M11 and M21. Depending on the interpolation method, the position shift amounts of temporally more separated pulses may be used. For example, Lanczos interpolation is a kind of multivariable interpolation. Lanczos interpolation is used to improve the sampling rate of a digital signal, and is known for best interpolation. Using a Lanczos kernel L(t) of Eq. 7, Lanczos interpolation for a 1D signal is performed by Eq. 8:

$$L(t) = \begin{cases} \operatorname{sinc}(t)\operatorname{sinc}\left(\frac{t}{a}\right) & \text{if } -a < t < a \\ 0 & \text{otherwise} \end{cases} \quad \text{Eq. 7}$$

-continued $$S(t) = \sum_{i=[t]-a+1}^{[t]+a} s_i L(t-i) \quad \text{Eq. 8}$$

Here, t is a time, a is a positive integer for determining a kernel size, $s_i$ is a sample of the 1D signal for a positive integer i, S(t) is an interpolated value, and [ ] is a floor function. It can be seen that, unlike linear interpolation, the position shift amounts of a plurality of pulses nearby, not only those of the nearest two pulses, are used for interpolation.

In such a manner, the position shift amount of a pulse of one wavelength can be calculated from the position shift amounts of temporally adjacent pulses of another wavelength. In that process, position shift correction on the plurality of wavelengths does not need to be performed, whereby the calculation time can be reduced.

A method for interpolating two 2D affine transformation matrices to calculate a 2D affine transformation matrix will be described as an example of a method for temporal interpolation.

Suppose that a signal group resulting from the pulsed light having the plurality of wavelengths is obtained. From the signals obtained by the irradiation with the pulsed light having the wavelength λ1 in the signal group, corresponding pulse volume data is obtained. Position shift correction based on an affine transformation is performed to calculate a position shift amount at the wavelength λ2 from the obtained pulse volume data of the wavelength λ1. The position shift amount at the wavelength λ2 is calculated as an affine transformation matrix with respect to the pulse volume data.

Suppose that there are two 2D affine transformation matrices A1 and A2. A1 is the position shift amount (affine transformation matrix) between pulse volume data $P_{\lambda 1,0}$ obtained by irradiation with the pulsed light having the wavelength λ1 at time t1 and pulse volume data $P_{\lambda 1,1}$ obtained by irradiation with the pulsed light having the wavelength λ1 at time t1+Δ. A2 is the position shift amount between the pulse volume data $P_{\lambda 1,1}$ obtained by irradiation with the pulsed light having the wavelength λ1 at time t1+Δ and pulse volume data $P_{\lambda 1,2}$ obtained by irradiation with the pulsed light having the wavelength λ1 at time t1+2Δ.

Suppose that an affine transformation matrix B to be determined is the position shift amount between pulse volume data $P_{\lambda 2,1/2}$ obtained by irradiation with the pulsed light having the wavelength λ2 at time t1+Δ/2 and pulse volume data $P\lambda_{2,3/2}$ obtained by irradiation with the pulsed light having the wavelength λ2 at time t1+3Δ/2.

A1 can be decomposed into a rotation component A1R and a scaling component A1S. Similarly, A2 can be decomposed into a rotation component A2R and a scaling component A2S. A rotation component BR of B can be obtained by temporally interpolating the elements of the matrices A1R and A2R. A scaling component BS of B can be obtained by temporally interpolating the elements of the matrices A1S and A2S. The resulting BR and BS can be integrated to calculate the position shift amount B.

Figure 9:
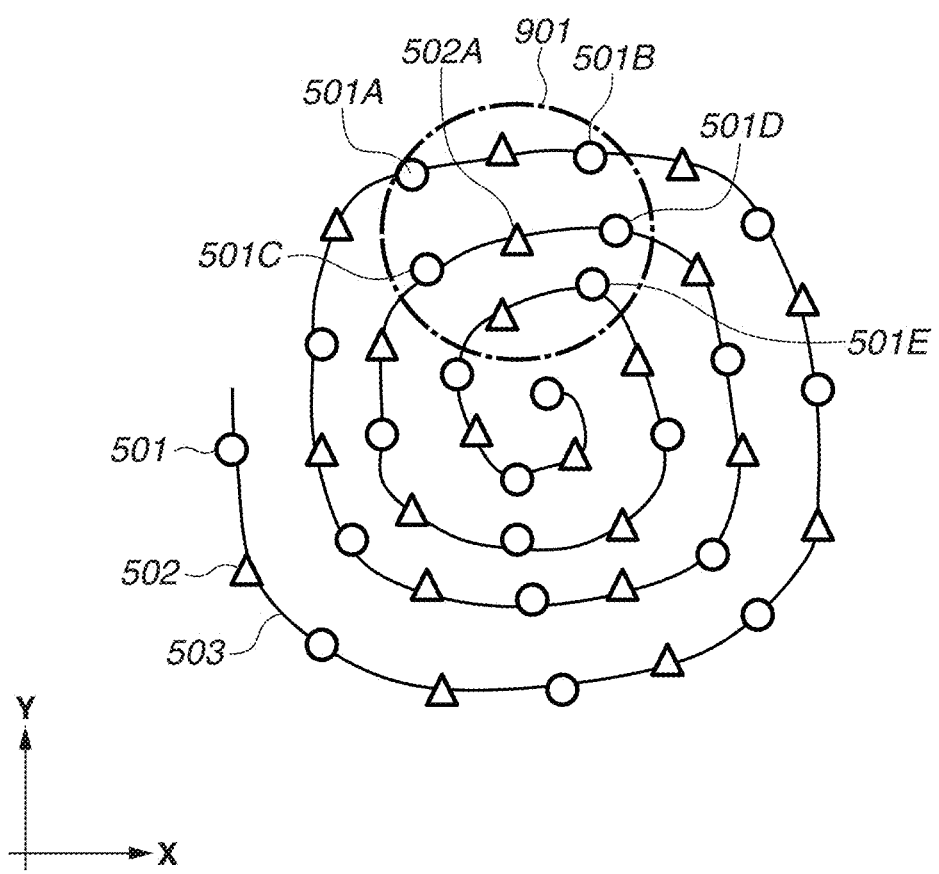
FIG. 9 is another diagram illustrating measurement points of the photoacoustic apparatus according to the first exemplary embodiment.

Spatial interpolation may be performed to calculate a position shift amount of a spatially adjacent pulse. FIG. 9 is a schematic diagram illustrating positions (measurement positions) of the probe 180 when the object 100 is irradiated with pulses of a plurality of wavelengths while being spatially scanned as in FIG. 5. A case in which the position shift information corresponding to the wavelength λ1 is spatially interpolated to obtain position shift information corresponding to a measurement position 502A corresponding to the timing of light irradiation with the wavelength λ2 will be described. The arithmetic unit 151 determines measurement positions at the wavelength λ1 corresponding to ones near the measurement position 502A. For example, the arithmetic unit 151 determines measurement positions at the wavelength λ1 within a predetermined distance from the measurement position 502A of the wavelength λ2. A dot-dashed line indicates a range 901 at the predetermined distance from the measurement position 502A. Measurement positions 501A, 501B, 501C, 501D, and 501E at the wavelength λ1 represent those at the wavelength λ1 within the predetermined distance from the measurement position 502A of the wavelength λ2. The arithmetic unit 151 then spatially interpolates the position shift information corresponding to the measurement positions 501A, 501B, 501C, 501D, and 501E at the wavelength λ1 to obtain the position shift information corresponding to the measurement position 502A at the wavelength λ2. As a method for spatial interpolation, a function may be fitted to the already-calculated position shift information, and the position shift information in the intended position may be determined from the function. As another method for spatial interpolation, the position shift information in the intended position may be calculated by assigning weights according to distance. In the following description, a method for calculating the position shift information about the pulse volume data to be calculated by assigning weights according to the distance to the position shift information about the pieces of pulse volume data within a predetermined distance from the measurement position to obtain the position shift information will be described.

Suppose that the positions irradiated with the pulses are at the center coordinates of the respective pieces of pulse volume data. The center coordinates of pulse volume data $P_{result}$ at the wavelength λ2 to calculate position shift information will be denoted as $POS_{result}$. The number of pulses of the position shift information about the pulse volume data at the wavelength λ1 within the range of a radius R mm from the center coordinates $POS_{result}$ is N. The position shift amounts (translation amounts) serving as the position shift information will be denoted as $M_i (1 \le i \le N)$.

The center coordinates will be denoted as $POS_i (1 \le i \le N)$.

A position shift amount $M_{result}$ of the pulse volume data $P_{result}$ can be calculated by the following Eq. 9:

$$M_{result} = \frac{\sum_{i=1}^{N} \omega_i M_i}{\sum_{i=1}^{N} \omega_i} \quad \text{Eq. 9}$$

For example, in FIG. 9, the measurement point 502A corresponds to the center coordinates $POS_{result}$ of the pulse volume data $P_{result}$ at the wavelength λ2 to calculate the position shift information. The range 901 has a radium of R mm from the measurement position 502A. The measurement positions 501A to 501E correspond to the center coordinates of the pieces of pulse volume data included in the range 901.

$\omega_i$ is a weight calculated from the distance. A spatial distance between $POS_i$ and $POS_{result}$ $$\overline{POS_iPOS_{result}}$$

can be used to calculate $\omega_i$ by the following Eq. 10:

$$\omega_i = \frac{1}{\overline{POS_iPOS_{result}}}, \text{ where } \overline{POS_iPOS_{result}} \leq R. \qquad \text{Eq. 10}$$

The spatial interpolation is not limited to the foregoing method, and any pieces of pulse volume data may be used for spatial interpolation. For example, nearest pieces of pulse volume data may be used. If the scanning is performed in a plurality of turns of spiral pattern, two adjacent pieces of pulse volume data on each turn may be used. The entire pulse volume data may be used.

In such a manner, from the position shift information corresponding to measurement positions spatially adjacent to a measurement position at a specific wavelength, position shift information about a piece of pulse volume data at another wavelength can be calculated.

The method for obtaining position shift information according to the present exemplary embodiment may be applied when light having three or more wavelengths is used for irradiation. In such a case, position shift information obtained at a specific wavelength can be used to obtain position shift information at the other plurality of wavelengths. Position shift information obtained at a plurality of wavelengths including one suitable for the acquisition of position shift information may be used to obtain position shift information at the other wavelength(s) In other words, position shift information obtained at one or more wavelengths can be used to determine position shift information at the other wavelength(s).

If position shift information taking consideration of deformation is obtained by using a deformable registration technique such as FFD, the position shift information may be a deformation field. The deformation field refers to a field of deformation from a deformable image to a reference image.

Figure 10:
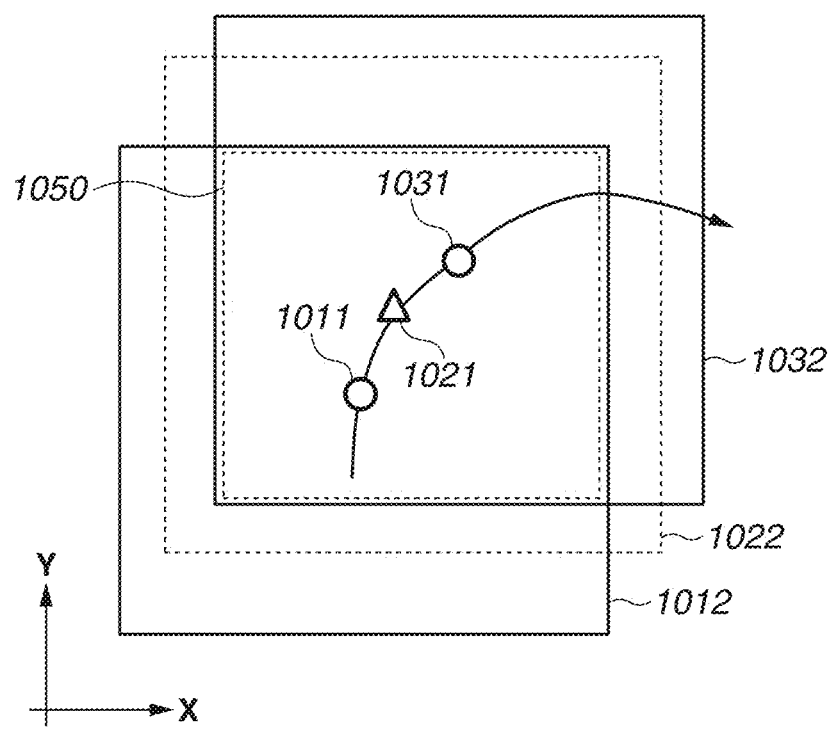
FIG. 10 is another diagram illustrating measurement points of the photoacoustic apparatus according to the first exemplary embodiment.

An example of a case in which the position shift information is a deformation field will be described with reference to FIG. 10. For the sake of simplicity, a three-dimensional image data area will be described on an XY 2D plane. Pulse irradiation positions 1011 and 1031 are pulse irradiation positions at the wavelength $\lambda 1$. Image data areas (images) 1012 and 1032 are ones of the respective pulses. A broken-lined area 1050 represents an overlapping area of the images 1012 and 1032. A pulse irradiation position 1021 is one at the wavelength $\lambda 2$. An image data area 1022 is an image data area corresponding to the pulse of the pulse irradiation position 1021. The pulse irradiation positions 1011, 1031, and 1021 are irradiated at times t1, t2, and (t1+t2)/2, respectively.

Suppose that deformable registration of the image 1012 with reference to the image 1032 is performed in the overlapping area 1050 of the images 1012 and 1032. In such a case, a three-dimensional deformation field having the size of the overlapping area 1050 can be calculated.

A deformation field of the overlapping area 1050 in the image data area 1022 can be calculated from the deformation field of the image 1012 with reference to the image 1032. The deformation field of the overlapping area 1050 can be calculated by temporally interpolating the deformation field of the image 1012 on the assumption that the deformation of the image 1012 with reference to the image 1032 occurs linearly with a lapse of time over a time t2−t1. More specifically, the deformation field of the overlapping area 1050 can be calculated by integrating the deformation for (t2−(t1+t2)/2)/(t2−t1).

In this example, a deformation field between two images is used to calculate a deformation field from either one of two images at an intermediate time. In such a manner, a deformation field of an image at one wavelength, captured between imaging times of two images at another wavelength having an overlapping area therebetween, can be calculated for each of the pieces of image data of pulses alternately emitted at a plurality of wavelengths. If such a calculation is applied to all the imaging pulses of the plurality of wavelengths, a deformation field for each pulse can be calculated with reference to the image data of any of the pulses at all the wavelengths.

In another example, if a plurality of deformation fields is already obtained between pieces of image data of a plurality of pulses, the plurality of deformation fields can be temporally interpolated to calculate a deformation field of a pulse emitted at an adjacent time. To calculate a deformation field, how each voxel in the plurality of deformation fields between the pieces of image data captured at discrete times is displaced is kept track of, focusing on the displace amount of a specific voxel in the image data in the deformation fields. A deformation field at a certain time may be calculated from the displacement amounts over time.

A wavelength at which the acquisition accuracy of the position shift information is high can be selected as a reference wavelength $\lambda 1$ for obtaining the position shift information. For example, the arithmetic unit 151 calculates an evaluation index for indicating image quality, such as resolution and a signal to noise ratio (SN), of the pulse volume data, combined volume data, and MIP images generated by using each of the plurality of wavelengths. The arithmetic unit 151 may obtain position shift information with a wavelength at which the calculated evaluation index indicating image quality is favorable as the wavelength $\lambda 1$.

If position shift information is obtained by temporal interpolation, the arithmetic unit 151 may determine the wavelength of light that is emitted a large number of times within a predetermined period, and set the wavelength as the wavelength $\lambda 1$. For example, the arithmetic unit 151 may set the wavelength of light that is emitted the largest number of times within a predetermined period as the wavelength $\lambda 1$ in the predetermined period. The arithmetic unit 151 may set the wavelength of light that is emitted more than a predetermined number of times within a predetermined period as the wavelength $\lambda 1$ in the predetermined period. A plurality of wavelengths may be set as the wavelength $\lambda 1$.

If the irradiation timing of the wavelengths may be regarded as being substantially the same, the position shift information corresponding to the irradiation timing of the light having wavelength $\lambda 1$ may be obtained as that corresponding to the irradiation timing of the light having the wavelength $\lambda 2$. For example, the position shift amounts obtained in step S300 may be simply used as those of the pulses of the other wavelength.

For example, if the irradiation intervals of the pulsed light between the plurality of wavelengths are as short as negligible with respect to the motion of the object 100, the irradiation timing of the wavelengths may be regarded as being substantially the same. For example, irradiation intervals at which the irradiation timings of the wavelengths can be regarded as being substantially the same with respect to the respiratory body motion of a living body will be described. Suppose that the living body makes linear displacements by respiration with a period of 3 seconds and a maximum displacement amount of 3 mm. If an allowable error of the resolution of a photoacoustic image is 0.25 mm, the irradiation timing between the wavelengths may be regarded as being substantially the same when the irradiation intervals are within 125 ms. Here, the displacement amount of the living body is assumed to be directly reflected on the error of the resolution of a photoacoustic image. If the allowable error of the resolution of a photoacoustic image is 0.1 mm, the irradiation timing between the wavelengths may be regarded as being substantially the same when the irradiation intervals are within 50 ms.

The arithmetic unit 151 may temporally or spatially interpolate the position shift information obtained in step S300 or S400 and use the resultant as position shift information about an image obtained by a different modality.

<Step S500: Step of Performing Position Shift Correction Based on Position Shift Information Corresponding to Irradiation Timings of Wavelength λ1 and Wavelength λ2>

In step S500, the arithmetic unit 151 performs position shift correction based on the position shift information corresponding to the wavelength λ1, obtained in step S300, and the position shift information corresponding to the wavelength λ2, obtained in step S400.

For example, the arithmetic unit 151 may perform processing for making position shift correction to the position information about the pulse volume data at the wavelength λ1, obtained in step S200, based on the position shift information corresponding to the wavelength 1, obtained in step S300. The arithmetic unit 151 may generate pulse volume data corresponding to the wavelength λ2 based on the signal group obtained in step S100. The arithmetic unit 151 may perform processing for correcting the position of the pulse volume data at the wavelength λ2 by a position shift amount based on the position shift information corresponding to the wavelength λ2, obtained in step S400. The arithmetic unit 151 may further perform registration by combining the pulse volume data of the wavelength λ1 and the pulse volume data of the wavelength λ2, of which position shifts are corrected, and thereby generate combined volume data.

An example of correcting a position shift of the pulse volume data at the wavelength λ1 will be described below. FIGS. 11A, 11B, 11C, 11D, and 11E illustrate an example of position shift correction processing (parallel processing) in the present step.

Figure 11A:
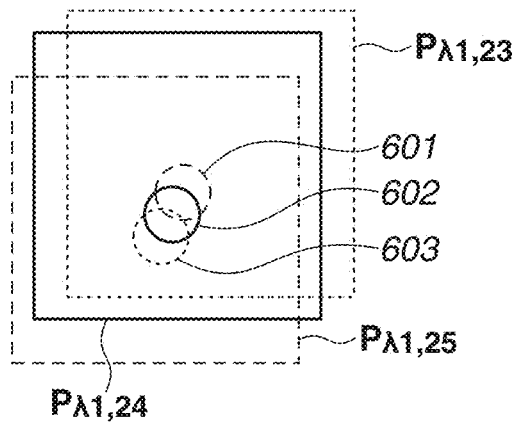
FIGS. 11A to 11E are diagrams illustrating position shift correction according to the first exemplary embodiment.

FIG. 11A illustrates part ($P_{\lambda 1,23}$ to $P_{\lambda 1,25}$) of pulse volume data before the parallel processing according to the present exemplary embodiment. The broken lines indicate the outer periphery of $P_{\lambda 1,25}$ and a feature 601 in $P_{\lambda 1,25}$. The solid lines indicate the outer periphery of $P_{\lambda 1,24}$ and a feature 602 therein. The dotted lines indicate the outer periphery $P_{\lambda 1,23}$ and a feature 603 therein. The features 601, 602, and 603 all represent the same feature. In the state of FIG. 11A, the features 601, 602, and 603 in the respective pieces of pulse volume data lie in different positions.

Figure 11B:
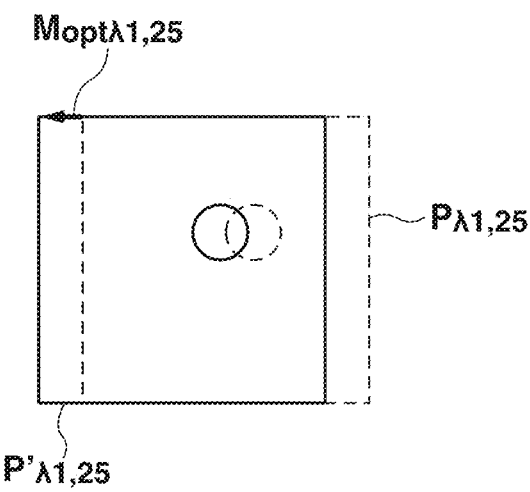
Figure 11C:
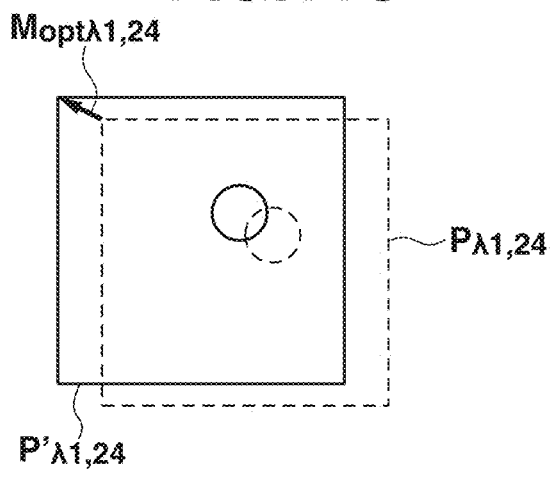

FIG. 11B illustrates pulse volume data $P'_{\lambda 1,25}$ obtained by translating the untranslated pulse volume data $P_{\lambda 1,25}$ by a position shift amount $Mopt_{\lambda 1,25}$ estimated by the foregoing method. FIG. 11C illustrates pulse volume data $P'_{\lambda 1,24}$ obtained by translating the untranslated pulse volume data $P_{\lambda 1,24}$ by a position shift amount $Mopt_{\lambda 1,24}$ estimated by the foregoing method.

Figure 11D:
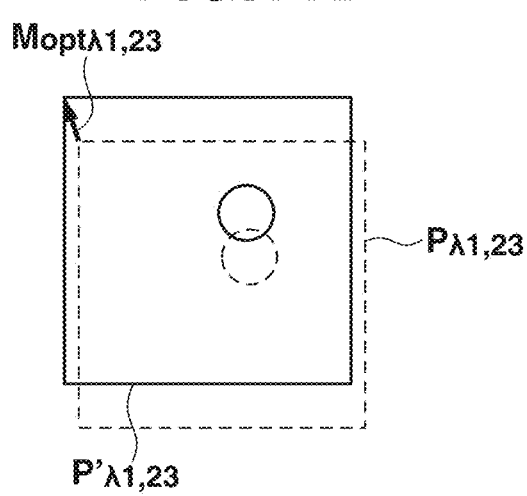

FIG. 11D illustrates pulse volume data $P'_{\lambda 1,23}$ obtained by translating the untranslated pulse volume data $P_{\lambda 1,23}$ by a position shift amount $Mopt_{\lambda 1,23}$ estimated by the foregoing method.

Figure 11E:
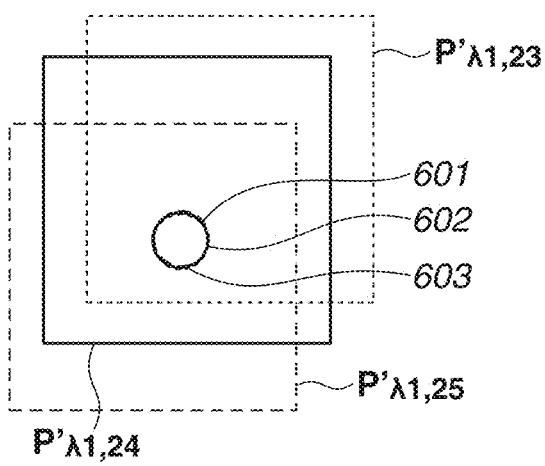

FIG. 11E illustrates a state in which the pieces of translated pulse volume data $P'_{\lambda 1,23}$, $P'_{\lambda 1,24}$, and $P'_{\lambda 1,25}$ are overlapped. In FIG. 11E, the features 601, 602, and 603 in the respective pieces of pulse volume data overlap at almost the same positions. The arithmetic unit 151 can combine the pieces of pulse volume data translated as illustrated in FIG. 11E to obtain registrated volume data. The registrated volume data is equivalent to combined volume data. "Registration" refers to performing both the position shift correction processing and the combination processing.

For example, in the reconstruction processing, the arithmetic unit 151 may perform processing for correcting the position information about the reception unit 120 corresponding to the irradiation timing at the wavelength λ1 by a position shift amount based on the position shift information corresponding to the wavelength λ1, obtained in step S300. In the reconstruction processing, the arithmetic unit 151 may perform processing for correcting the position information about the reception unit 120 corresponding to the irradiation timing at the wavelength λ2 by a position shift amount based on the position shift information corresponding to the wavelength λ2, obtained in step S400. Then, the arithmetic unit 151 may perform the reconstruction processing to generate combined volume data based on the signal groups obtained in step S100 and the position information about the reception unit 120 of which the position shifts corresponding to the irradiation timing at the wavelengths λ1 and λ2 are corrected.

Now, an example of a method for performing position shift correction on the position information about the reception unit 120 will be described. First, the arithmetic unit 151 obtains position information about the reception unit 120 with no position shift taken into consideration. For example, the arithmetic unit 151 may obtain the position information with no position shift taken into consideration by reading the position information about the reception unit 120 during light irradiation, stored in the storage unit 152 in advance. The arithmetic unit 151 may obtain the position information about the reception unit 120 with no position shift taken into consideration by receiving the position information about the reception unit 120 from the position sensor included in the driving unit 130, with light irradiation as a trigger.

The arithmetic unit 151 then corrects (e.g., performs translation processing on) the position information about the reception unit 120 during the light irradiation with no position shift taken into consideration by the position shift amounts indicated by the position shift information obtained in step S300 or S400. The arithmetic unit 151 can thereby obtain the position information about the reception unit 120 of which position shifts during the light irradiation are corrected. In other words, the arithmetic unit 151 can obtain the position shift-corrected position information about the reception unit 120 based on the position shift information obtained in step S300 or S400.

The arithmetic unit 151 obtains combined image data based on the signal groups obtained in step S100 and the position shift-corrected position information about the reception unit 120. In the present step, the arithmetic unit 151 may reconstruct an area smaller than the entire imaging area from a signal corresponding to one round of light irradiation. The arithmetic unit 151 may repeat such reconstruction for a plurality of times of light irradiation to generate a piece of volume data. In such a case, in the present step, the arithmetic unit 151 obtains a plurality of pieces of pulse volume data corresponding to a plurality of times of light irradiation, and combines the image data groups. The arithmetic unit 151 may generate a piece of volume data by reconstructing the entire imaging area from the signal group corresponding to the plurality of times of light irradiation.

The arithmetic unit 151 may perform processing similar to the foregoing processing when performing combination processing of data corresponding to a plurality of wavelengths. The combination processing of data corresponding to a plurality of wavelengths includes addition processing and averaging processing of the data corresponding to the plurality of wavelengths, as well as processing for performing comparison calculations on the data corresponding to the plurality of wavelengths to obtain functional information such as oxygen saturation. A method for obtaining oxygen saturation serving as functional information by using data corresponding to a plurality of wavelengths will be described below.

Suppose that at the wavelengths λ1 and λ2, light absorption other than that of hemoglobin is as low as negligible. Using the molecular absorption coefficient of oxyhemoglobin and that of deoxyhemoglobin, absorption coefficients at the wavelengths λ1 and λ2 are expressed by Eqs. 11 and 12:

$$\mu_a(\lambda_1) = \varepsilon_{ox}(\lambda_1)C_{ox} + \varepsilon_{de}(\lambda_1)C_{de}, \text{ and} \quad \text{Eq. 11}$$

$$\mu_a(\lambda_2) = \varepsilon_{ox}(\lambda_2)C_{ox} + \varepsilon_{de}(\lambda_2)C_{de}. \quad \text{Eq. 12}$$

Here, $\mu_a(\lambda_1)$ is the absorption coefficient for the light having the wavelength λ1 at position (i, j, k), and $\mu_a(\lambda_2)$ is the absorption coefficient for the light having the wavelength λ2 in position (i, j, k). Both the absorption coefficients $\mu_a(\lambda_1)$ and $\mu_a(\lambda_2)$ can be expressed in units of [mm$^{-1}$]. $C_{ox}$ is the amount of oxyhemoglobin [mol]. $C_{de}$ is the amount of deoxyhemoglobin [mol]. Both $C_{ox}$ and $C_{de}$ indicate values at position (i, j, k).

$\varepsilon_{ox}(\lambda_1)$ and $\varepsilon_{de}(\lambda_1)$ are respectively the molecular absorption coefficients [mm$^{-1}$·mol$^{-1}$] of oxyhemoglobin and deoxyhemoglobin at the wavelength λ1. $\varepsilon_{ox}(\lambda_2)$ and $\varepsilon_{dc}(\lambda_2)$ are respectively the molecular absorption coefficients [mm$^{-1}$·mol$^{-1}$] of oxyhemoglobin and deoxyhemoglobin at the wavelength λ2. $\varepsilon_{ox}(\lambda_1)$, $\varepsilon_{dc}(\lambda_1)$, $\varepsilon_{ox}(\lambda_2)$, and $\varepsilon_{de}(\lambda_2)$ can be obtained in advance by measurement or from literature data.

Both $C_{ox}$ and $C_{de}$ can be determined by solving the simultaneous equations of Eqs. 11 and 12, using the molecular absorption coefficients $\varepsilon_{ox}(\lambda_1)$, $\varepsilon_{de}(\lambda_1)$, $\varepsilon_{ox}(\lambda_2)$, and $\varepsilon_{de}(\lambda_2)$, and the absorption coefficients $\mu_a(\lambda_1)$ and $\mu_a(\lambda_2)$. If the number of wavelengths used is large, the least squares method may be used. An oxygen saturation SO$_2$ is defined as the rate of oxyhemoglobin in total hemoglobin, as expressed by Eq. 13. Therefore, based on Eqs. 11, 12, and 13, the oxygen saturation SO$_2$ can be expressed as Eq. 14.

According to Eq. 14, the arithmetic unit 151 can obtain the oxygen saturation SO$_2$ at position (i, j, k) based on the molecular absorption coefficients $\varepsilon_{ox}(\lambda_1)$, $\varepsilon_{de}(\lambda_1)$, $\varepsilon_{ox}(\lambda_2)$, and $\varepsilon_{de}(\lambda_2)$, and the absorption coefficients $\mu_a(\lambda_1)$ and $\mu_a(\lambda_2)$.

$$SO_2 = \frac{C_{ox}}{C_{ox} + C_{de}} \quad \text{Eq. 13}$$

$$SO_2 = \frac{\frac{\mu_a(\lambda_2)}{\mu_a(\lambda_1)} \cdot \varepsilon_{de}(\lambda_1) - \varepsilon_{de}(\lambda_2)}{(\varepsilon_{ox}(\lambda_2) - \varepsilon_{de}(\lambda_2)) - \frac{\mu_a(\lambda_2)}{\mu_a(\lambda_1)} \cdot (\varepsilon_{ox}(\lambda_1) - \varepsilon_{de}(\lambda_1))} \quad \text{Eq. 14}$$

Such processing can be performed on a plurality of positions to determine the oxygen saturation at the plurality of positions and obtain an oxygen saturation distribution.

The oxygen saturation distribution is obtained by comparison calculation (e.g., processing for calculating a ratio) of absorption coefficient distributions. If the absorption coefficients of the plurality of wavelengths have relatively correct values, an appropriate oxygen saturation distribution can be obtained. The absorption coefficient distributions therefore do not need to be accurately determined in terms of absolute values.

In the foregoing description, an initial sound pressure image with a reduced effect of position shift is calculated, and absorption coefficient images and an oxygen saturation image are calculated from the initial sound pressure image. However, the method is not limited thereto. Pulse volume data of a plurality of wavelengths may be determined as absorption coefficient distribution images, and position shift amounts may be calculated from the absorption coefficient distribution image of one of the wavelengths. The position shift amounts calculated in such a manner may be applied to cases of the other wavelength to calculate an absorption coefficient image with a reduced effect of position shift, and calculate an oxygen saturation image from the absorption coefficient images.

In such a manner, absorption coefficient images with a reduced effect of position shift can be obtained from between the images of the plurality of wavelengths. The absorption coefficient images with a reduced effect of position shift can then be combined to calculate an oxygen saturation image.

In the present step, image data (registrated volume data) in which the effect of variations in the relative positional relationship of the object 100 and the reception unit 120 of photoacoustic waves between the rounds of light irradiation is suppressed can be obtained.

The foregoing processing is applicable even if the reception unit 120 does not move between the rounds of light irradiation. In other words, the foregoing processing is applicable even if the photoacoustic apparatus does not include the driving unit 130. Even in such a case, image data in which the effect of variations in the relative positional relationship between the object 100 and the reception unit 120 of photoacoustic waves between a plurality of times of light irradiation is suppressed can be obtained.

If a modality different from the photoacoustic apparatus (e.g., ultrasonographic apparatus) is used for imaging along with the imaging using the photoacoustic apparatus, the position shift information obtained by the photoacoustic apparatus may be used to obtain position shift information about the other modality. For example, the arithmetic unit 151 may temporally or spatially interpolate the position shift information obtained in step S300, S400, or S500 to obtain position shift information about image data obtained by the other modality. If the photoacoustic apparatus and the other modality generate image data at substantially the same position at substantially the same time, the position shift information obtained by the photoacoustic apparatus may be used as that of the other modality.

For example, if an ultrasonographic apparatus is assumed as the other modality, an inspection system including the photoacoustic apparatus includes a transmission and reception unit of ultrasonic waves. The transmission and reception unit transmits ultrasonic waves to the object 100, and receives echo waves of the transmitted ultrasonic waves to output an ultrasonic signal. The transmission and reception unit includes a transducer that receives acoustic waves to output an electrical signal. The transmission and reception unit may include a plurality of transducers. The transmission and reception unit may provide a transducer for transmitting ultrasonic waves separately from a transducer for receiving acoustic waves. A transducer for transmitting ultrasonic waves and a transducer for receiving acoustic waves may be constituted by the same transducer. A transducer for transmitting and receiving ultrasonic waves may be provided separately from a transducer for receiving photoacoustic waves. A transducer for transmitting and receiving ultrasonic waves and a transducer for receiving photoacoustic waves may be constituted by the same transducer.

A configuration and processing of a photoacoustic apparatus according to a second exemplary embodiment will be described below. The second exemplary embodiment uses a photoacoustic apparatus similar to that of the first exemplary embodiment. In the second exemplary embodiment, components similar to those of the photoacoustic apparatus according to the first exemplary embodiment will be designated by the same reference numerals. Thus, a detailed description thereof will be omitted.

As described above, if light having a plurality of wavelengths is used, the plurality of wavelengths may include a wavelength at which the estimation accuracy of a position shift between a plurality of pieces of image data is low. In such a case, the position shift information corresponding to the irradiation timing of the light of that wavelength is unable to be accurately obtained by using only an image data group obtained at the wavelength. In other words, if light having a plurality of wavelengths is used, the estimation accuracy of a position shift may vary from one wavelength to another.

Then, the photoacoustic apparatus according to the present exemplary embodiment of the present invention obtains position shift information between a plurality of pieces of image data at each of a plurality of mutually different wavelengths. The pieces of position shift information obtained at the respective plurality of wavelengths are then combined to update the position shift information obtained before. Consequently, even if a wavelength at which estimation accuracy is low is included, the obtained position shift information is updated by also using the position shift information obtained at a wavelength at which the estimation accuracy of a position shift is relatively high. Thus, the position shift information can be obtained with high accuracy.

More specifically, the photoacoustic apparatus according to the present exemplary embodiment irradiates the object 100 with light having mutually different first and second wavelengths a plurality of times each. A first image data group corresponding to the first wavelength is then generated, and position shift information (first position shift information) between the pieces of image data in the first image data group is obtained. The position shift information obtained at that time corresponds to the amount of variation (position shift amount) in the relative position between the object 100 and the probe 180 corresponding to the irradiation timing of the light having the first wavelength. A second image data group corresponding to the second wavelength is also generated, and position shift information (second position shift information) between the pieces of image data in the second image data group is obtained. Based on the first position shift information and the second position shift information, the position shift information corresponding to the light irradiation timings of the first and second wavelengths is updated. Since the position shift information obtained at the wavelength at which the estimation accuracy of a position shift is high is also used in obtaining the position shift information at the wavelength at which the estimation accuracy of a position shift is low, variations in the estimation accuracy of a position shift between the wavelengths decrease.

In addition, when the pieces of position shift information at the respective wavelengths are combined, weights on the pieces of position shift information can be changed to give priority to the estimation result at the wavelength of high estimation accuracy.

As a method for obtaining the signal group and the acquisition of the position shift information corresponding to the light irradiation timing of each wavelength, the methods described in the first exemplary embodiment may be applied.

An operation of the photoacoustic apparatus, including information processing according to the present exemplary embodiment, will be described below with reference to the flowchart illustrated in FIG. 12. Steps similar to those illustrated in FIG. 4 are designated by the same reference numerals. Thus, a detailed description thereof will be omitted.

<Step S210: Step of Obtaining Image Data Group Corresponding to Wavelength λ2>

In step S210, like in step S200, the arithmetic unit 151 obtains an image data group corresponding to the light irradiation of the wavelength λ2 based on the signal group obtained in step S100.

<Step S310: Step of Obtaining Position Shift Information Corresponding to Irradiation Timing of Light Having Wavelength λ2>

In step S310, like in step S300, the arithmetic unit 151 obtains position shift information corresponding to the irradiation timing of the light having the wavelength λ2 based on the image data group corresponding to the wavelength λ2, obtained in step S210.

<Step S600: Step of Updating Position Shift Information Based on Position Shift Information Corresponding to Irradiation Timings of Light Having Wavelength λ1 and Wavelength λ2>

In step S600, the arithmetic unit 151 updates the pieces of position shift information based on the position shift information corresponding to the irradiation timing of the light having the wavelength λ1, obtained in step S300, and the position shift information corresponding to the irradiation timing of the light having the wavelength λ2, obtained in step S310.

For example, suppose that the arithmetic unit 151 calculates a translation amount $Mopt\_st_{\lambda 1}$ as the position shift information corresponding to the irradiation timing of the light having the wavelength λ1 in step S300, and calculates a translation amount $Mopt\_st_{\lambda 2}$ as the position shift information corresponding to the irradiation timing of the light having the wavelength λ2 in step S310. In such a case, in the present step, the arithmetic unit 151 may update the position shift information $Mopt\_st_{\lambda 1}$ and $Mopt\_st_{\lambda 2}$ of the respective wavelengths by averaging the pieces of position shift information as expressed by Eq. 15:

$$Mopt\_st_{\lambda 1}=(Mopt_{\lambda 1}+Mopt_{\lambda 2})/2, \text{ and}$$

$$Mopt\_st_{\lambda 2}=(Mopt_{\lambda 1}+Mopt_{\lambda 2})/2 \qquad \text{Eq. 15}$$

Using the position shift information at the respective wavelengths, the arithmetic unit 151 may update the position shift information for the respective wavelengths by temporal or spatial interpolation as described in the first exemplary embodiment.

The arithmetic unit 151 may update the position shift information of the respective wavelengths by assigning weights to the pieces of position shift information of the respective wavelengths. The arithmetic unit 151 may update the position shift information for the respective wavelengths by weighting the pieces of position shift information for the respective wavelengths with predetermined weights. The arithmetic unit 151 may weight the pieces of position shift information for the respective wavelengths with weights that are determined according to instructions given by the user using the input unit 170.

<Step S700: Step of Performing Position Shift Correction Based on Updated Position Shift Information>

In step S700, the arithmetic unit 151 performs position shift correction by a method similar to that described in step S500, based on the position shift information corresponding to the irradiation timings of the light having the wavelength $\lambda 1$ and the wavelength $\lambda 2$, updated in step S600.

The present exemplary embodiment uses the position shift information that is combined by using not only the position shift information obtained at the wavelength at which the estimation accuracy of a position shift is low but also the position shift information obtained at the wavelength at which the estimation accuracy of a position shift is high. This reduces variations in the estimation accuracy of a position shift between the wavelengths.

FIG. 13 is a schematic diagram illustrating a GUI including a slider for determining weights on the pieces of position shift information for the respective wavelengths. For example, the GUI illustrated in FIG. 13, displayed on the display unit 160, can be used to determine weights.

A GUI 1001 displays a display area 1002 of a photoacoustic image, a graph 1003 of the position shift amount at the wavelength $\lambda 1$, and a graph 1004 of the position shift amount at the wavelength $\lambda 2$. The vertical axes of the graphs 1003 and 1004 indicate the position shift amounts. The horizontal axes indicate the pulse index. In other words, the graphs 1003 and 1004 are plots of the position shift amounts with respect to the pulse volume data for the wavelengths $\lambda 1$ and $\lambda 2$. A slider bar 1007 is an item for determining the weights on the position shift amounts for the plurality of wavelengths. If the slider bar 1007 is moved to the left, the position shift amount at the wavelength $\lambda 1$ is more dominantly added. If the slider bar 1007 is moved to the right, the position shift amount of the wavelength $\lambda 2$ is more dominantly added. In other words, moving the slider bar 1007 to the left increases the weight for the wavelength $\lambda 1$, and moving the slider bar 1007 to the right increases the weight for the wavelength $\lambda 2$, whereby weighted final position shift amounts are determined. The display area 1002 displays a photoacoustic image obtained by using the weighted final position shift amounts. If the user operates the slider bar 1007, the final position shift amounts are recalculated and updated. A photoacoustic image is then obtained again by using the updated position shift amounts, and the photoacoustic image displayed in the display area 1002 is updated. In FIG. 13, a photoacoustic image 1008 of a foot is displayed in the display area 1002. The photoacoustic image 1008 includes a blood vessel image 1009.

Using such a GUI to change and determine the weights on the position shift amounts for the plurality of wavelengths by the slider bar 1007, the user can determine the final position shift amounts while observing a change in the image quality (e.g., resolution) of the photoacoustic image displayed in the display area 1002.

A configuration and processing of a photoacoustic apparatus according to a third exemplary embodiment will be described below. The third exemplary embodiment uses a photoacoustic apparatus similar to that of the first or second exemplary embodiment. In the third exemplary embodiment, components similar to those of the photoacoustic apparatus according to the first or second exemplary embodiment will be designated by the same reference numerals. Thus, a detailed description thereof will be omitted.

As described above, if light having a plurality of mutually different wavelengths is used, image characteristics such as an image intensity may vary from one wavelength to another. In such a case, the estimation accuracy of a position shift can drop due to a difference in the image intensity between the wavelengths.

The photoacoustic apparatus according to the present exemplary embodiment then generates image data resulting from light of a respective plurality of mutually different wavelengths based on photoacoustic waves generated by the light irradiation with the respective wavelengths. After processing for reducing a difference in the image characteristics between the wavelengths is performed, position shift information is obtained by using an image data groups at the plurality of wavelengths. This can suppress a drop in the estimation accuracy of a position shift due to a difference in the image characteristics between the wavelengths.

More specifically, the photoacoustic apparatus according to the present exemplary embodiment irradiates the object 100 with light having mutually different first and second wavelengths a plurality of times each. A first image data group corresponding to the first wavelength is then generated. A second image data group corresponding to the second wavelength is also generated. Image processing is performed on at least one of the first and second image data groups to reduce a difference in the image characteristics between the first and second image data groups. Position shift information corresponding to the light irradiation timings of the first and second wavelengths is then obtained by using the first and second image data groups after the processing for reducing a difference in the image characteristics.

In the foregoing description, a difference in the image characteristics between the wavelengths is described to be reduced by the image processing on the image data. However, signal processing that is performed on a signal before formation of the image data may result in the reduction of a difference in the image characteristic between the wavelengths.

Figure 14:
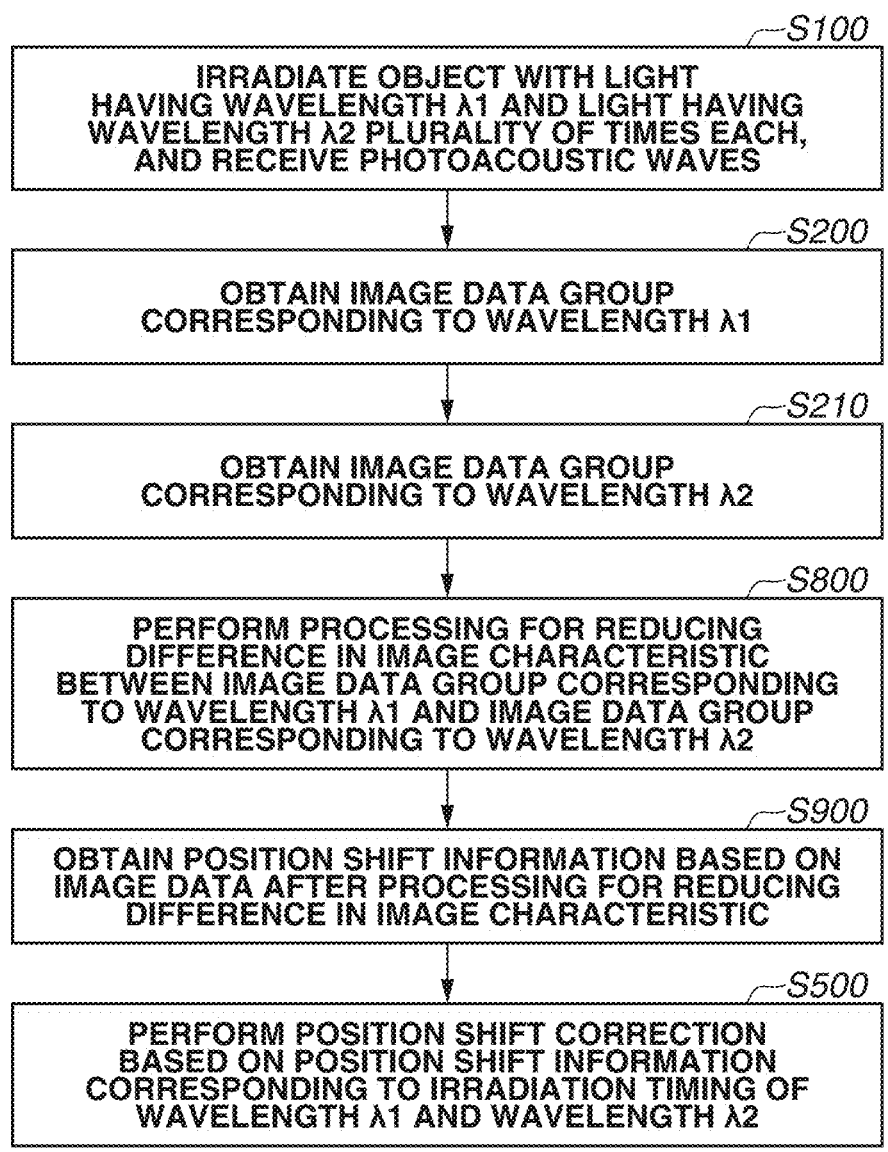
FIG. 14 is a flowchart illustrating an operation of a photoacoustic apparatus according to a third exemplary embodiment.

An operation of the photoacoustic apparatus, including information processing according to the present exemplary embodiment, will be described below with reference to the flowchart illustrated in FIG. 14. Steps similar to those illustrated in FIG. 4 are designated by the same reference numerals. Thus, a detailed description thereof will be omitted.

<Step S800: Step of Performing Processing for Reducing Difference in Image Characteristics Between Image Data Group Corresponding to Wavelength $\lambda 1$ and Image Data Group Corresponding to Wavelength $\lambda 2$>

In step S800, the arithmetic unit 151 performs image processing on the image data group at the wavelength $\lambda 1$, obtained in step S200, and the image data group at the wavelength $\lambda 2$, obtained in step S210, to reduce a difference in the image characteristics between the image data group of the wavelength $\lambda 1$ and the image data group of the wavelength $\lambda 2$. Examples of the processing for reducing a difference in the image characteristics between the wavelengths include processing for equalizing the maximum values or minimum values of the image intensity and processing for making the image intensities of the plurality of wavelengths nearly equal in terms of an image average or variance. As employed herein, the processing for reducing a difference in the image characteristics between pieces of image data will be referred to as normalization processing.

An example of normalizing the image intensity of image data will be described. First, the arithmetic unit 151 determines a maximum value valmax (one value for all the pulses) of the image intensity of all the pulse volume data obtained in steps S200 and S300. The arithmetic unit 151 rounds values of the image intensity of the pulse volume data smaller than 0 to 0. Then, the arithmetic unit 151 normalizes image intensities $P_{x,y,z}$ of the voxels of the pulse volume data so that the determined maximum value valmax of the image intensity becomes a predetermined value val. In other words, the arithmetic unit 151 normalizes the pulse volume data as expressed by Eq. 16:

$$P'_{x,y,z} = P_{x,y,z} * \text{val/valmax}. \qquad \text{Eq. 16}$$

$P'_{x,y,z}$ is the value of the normalized image intensity of each voxel. While the normalization is performed so as to set the maximum value valmax of the pulse volume data of the plurality of wavelengths to be a predetermined value val, the maximum value valmax may be determined for each wavelength and normalization may be performed so as to set the maximum value valmax to be a predetermined value val. The arithmetic unit 151 may obtain a minimum value of the pulse volume data without rounding the values smaller than 0 to 0, and convert the intensities between the minimum and maximum values into values of 0 to val. Alternatively, the intensities between the minimum and maximum values may be converted into values of val' to val. In other words, the image intensities may be normalized to fall within a desired range of numerical values. Any method may be used for normalization as long as a difference in the image intensity between the wavelengths is reduced.

Alternatively, the images may be normalized so that the image intensities have specific values such as an average of 0 and a variance of 1. The images may be normalized so that the image intensities have an average and variance of specific values other than 0 or 1.

<Step S900: Step of Obtaining Position Shift Information Based on Image Data after Processing for Reducing Difference in Image Characteristics>

In step S900, the arithmetic unit 151 obtains position shift information associated with the light irradiation timings of the first and second wavelengths based on the image data groups for the wavelengths $\lambda 1$ and $\lambda 2$ after the processing for reducing a difference in the image characteristics between the wavelengths in step S800. As a method for obtaining the position shift information by using the image data, a method similar to that described in step S300 may be employed.

In such a manner, the image data groups of which a difference in the image characteristics between the wavelengths is reduced can be used to suppress a drop in the estimation accuracy of a position shift due to a difference in the image characteristics between the wavelengths. In step S500, the arithmetic unit 151 can perform position shift correction with high accuracy by using the position shift information obtained in this manner.

In the present exemplary embodiment, the image data groups are described to be generated for the respective wavelengths. However, even if an image data group is not generated for one wavelength, the method for obtaining position shift information described in the present exemplary embodiment can be applied as long as image data groups are generated.

A configuration and processing of a photoacoustic apparatus according to a fourth exemplary embodiment will be described below. The fourth exemplary embodiment uses a photoacoustic apparatus similar to that of the first, second, or third exemplary embodiment. In the fourth exemplary embodiment, components similar to those of the photoacoustic apparatus according to the first, second, or third exemplary embodiment will be designated by the same reference numerals. Thus, a detailed description thereof will be omitted.

In the present exemplary embodiment, an example of performing at least one of the methods for obtaining position shift information described in the first, second, and third exemplary embodiments based on the user's instructions given by using the input unit 170 will be described.

Figure 15:
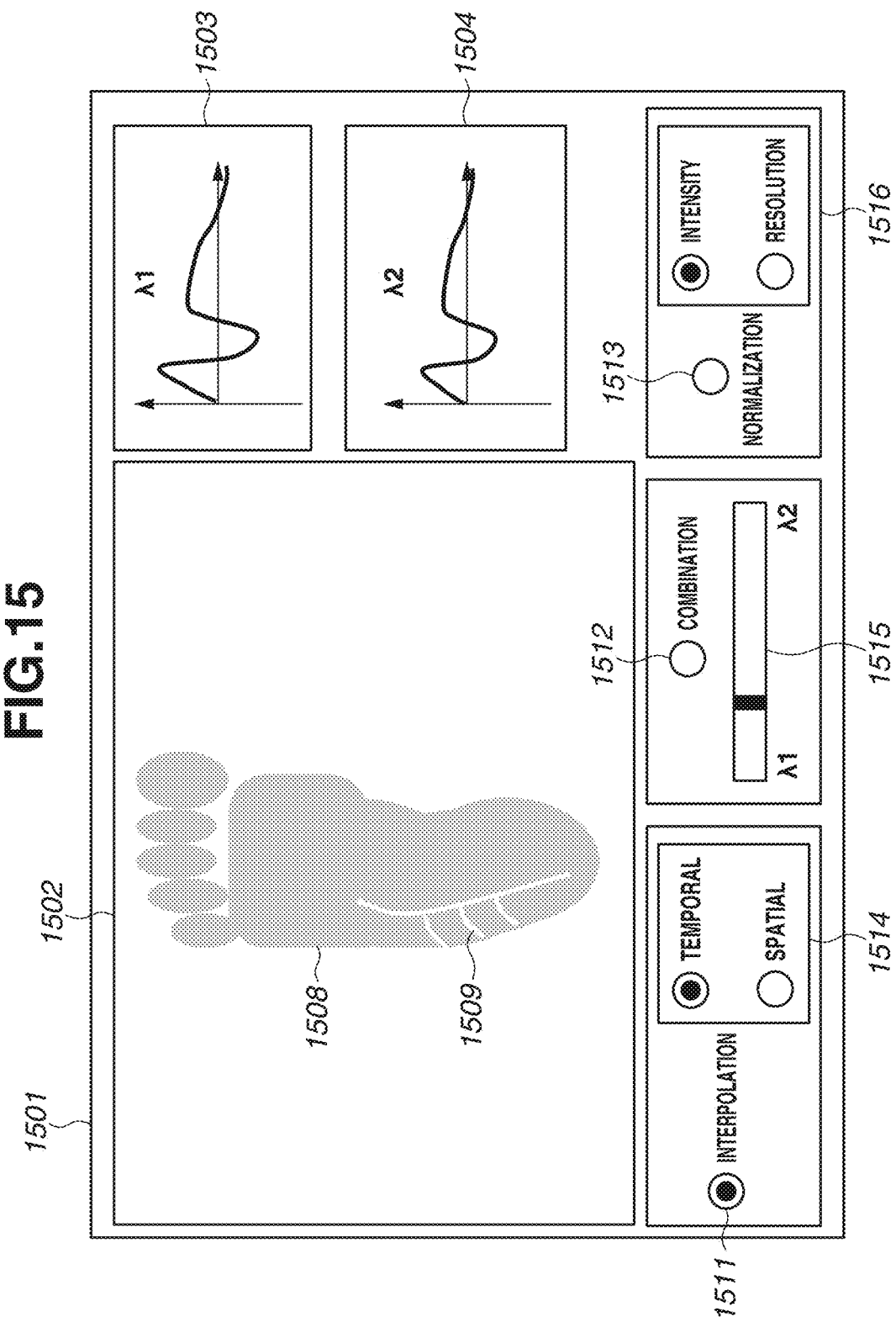
FIG. 15 is a diagram illustrating a GUI according to a fourth exemplary embodiment.

FIG. 15 illustrates a GUI displayed on the display unit 160 according to the present exemplary embodiment. A GUI 1501 displays a display area 1502 of a photoacoustic image, a graph 1503 of the position shift amount for the wavelength $\lambda 1$, and a graph 1504 of the position shift amount for the wavelength $\lambda 2$. The vertical axes of the graphs 1503 and 1504 indicate the position shift amounts. The horizontal axes indicate the pulse index. In other words, the graphs 1503 and 1504 are plots of the position shift amounts with respect to the pulse volume data for the wavelengths $\lambda 1$ and $\lambda 2$. In FIG. 15, a photoacoustic image 1508 of a foot is displayed in the display area 1502. The photoacoustic image 1508 includes a blood vessel image 1509.

The user selects a desired acquisition method from selection buttons 1511, 1512, and 1513 of acquisition methods of position shift information by using the input unit 170.

The selection button 1511 is a radio button corresponding to the method, in which position shift information corresponding to a specific wavelength described in the first exemplary embodiment is used to obtain position shift information corresponding to another wavelength. In the present exemplary embodiment, if the selection button 1511 is selected, the arithmetic unit 151 enters a mode in which the position shift information corresponding to the wavelength $\lambda 1$ is interpolated to obtain position shift information corresponding to the wavelength $\lambda 2$. For the interpolation method, the user can select either one of selection buttons 1514 to determine whether the arithmetic unit 151 performs temporal interpolation or spatial interpolation.

The selection button 1512 is a radio button corresponding to the method, in which pieces of position shift information corresponding to a respective plurality of wavelengths described in the second exemplary embodiment are combined to update the pieces of position shift information. In the present exemplary embodiment, if the selection button 1512 is selected, the arithmetic unit 151 enters a mode of assigning weights to and combining the position shift information corresponding to the wavelength $\lambda 1$ and the position shift information corresponding to the wavelength $\lambda 2$. If the user operates a slider bar 1515, the weights on the respective pieces of position shift information can be changed. The slider bar 1515 has a function similar to that of the slider bar 1007.

The selection button 1513 is a radio button corresponding to the method described in the third exemplary embodiment, in which position shift information is obtained after the normalization processing for reducing a difference in the image characteristics between the wavelengths. In the present exemplary embodiment, if the selection button 1513 is selected, the arithmetic unit 151 enters a mode of performing the normalization processing on the data obtained based on the light having the wavelength $\lambda 1$ and the data obtained based on the light having the wavelength λ2. For the method of the normalization processing, the user can select either one of selection buttons 1516 to determine whether the arithmetic unit 151 performs normalization processing for reducing a difference in image intensity or normalization processing for reducing a difference in resolution.

In such a manner, the user can select a desired method for obtaining position shift information and observe a photoacoustic image to which the selected position shift information is applied. Thus, the user can check combined image data obtained by a method for obtaining position shift information suitable for the characteristics of the image data.

Other Exemplary Embodiments

An exemplary embodiment of the present invention may be implemented by executing the following processing. The processing includes supplying software (program) for implementing the functions of the foregoing exemplary embodiments to a system or an apparatus via a network or various storage media, and reading and executing the program by a computer (or a CPU or a micro processing unit (MPU)) of the system or apparatus.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-188417, filed Sep. 27, 2016, which is hereby incorporated by reference herein in its entirety.

What is claimed is:

1. A photoacoustic apparatus comprising a processing unit configured to:
   obtain first image data generated based on an acoustic wave generated by irradiating an object with a first light having a first wavelength;
   obtain second image data generated based on an acoustic wave generated by irradiating the object with a second light having a second wavelength different from the first wavelength;
   perform normalization processing on at least one of the first image data and the second image data so as to decrease a difference in an image characteristic between the first image data and the second image data; and
   obtain position shift information associated with a plurality of timings of the first light and the second light on the basis of the first and second image data at least one of which is subjected to the normalization processing.

2. The photoacoustic apparatus according to claim 1, wherein the processing unit is configured to:
   obtain a signal group generated by a reception unit receiving the acoustic waves generated by irradiating the object with the first light and the second light; and
   generate combined image data based on the position shift information and the signal group.

3. The photoacoustic apparatus according to claim 1, wherein the processing unit is configured to:
   correct a position shift of the first image data on the basis of the position shift information;
   correct a position shift of the second image data on the basis of the position shift information; and
   generate combined image data on the basis of the position shift-corrected first and second image data.

4. The photoacoustic apparatus according to claim 1, wherein the processing unit is configured to:
   obtain a signal group generated by a reception unit receiving the acoustic waves generated by irradiating the object with the first light and the second light;
   obtain first position information about the reception unit associated with irradiation timing of the first light; and
   generate the first image data by using the first position information and the signal group.

5. The photoacoustic apparatus according to claim 1, wherein the processing unit is configured to:
   obtain a signal group generated by a reception unit receiving the acoustic waves generated by irradiating the object with the first light and the second light;
   obtain first position information about the reception unit associated with irradiation timing of the first light;
   correct a position shift of the first position information on the basis of the position shift information;
   obtain second position information about the reception unit corresponding to irradiation timing of the second light;
   correct a position shift of the second position information on the basis of the position shift information; and
   obtain combined image data on the basis of the position shift-corrected first and second position information and the signal group.

6. The photoacoustic apparatus according to claim 2, wherein the processing unit is configured to generate data indicating a spatial distribution of oxygen saturation as the combined image data.

7. The photoacoustic apparatus according to claim 1, wherein the processing unit is configured to change an image intensity of at least one of the first image data and the second image data so as to decrease a difference in the image intensity between the first image data and the second image data.

8. The photoacoustic apparatus according to claim 7, wherein the processing unit is configured to determine a maximum value of the image intensity of the first image data and the second image data, and change the image intensity of at least one of the first image data and the second image data so as to cause the maximum value to be a predetermined value.

9. The photoacoustic apparatus according to claim 7, wherein the processing unit is configured to change the image intensity of at least one of the first image data and the second image data so as to cause a numerical range of the image intensity of the first image data and the second image data to be a predetermined numerical range.

10. The photoacoustic apparatus according to claim 1, wherein the processing unit is configured to change resolution of at least one of the first image data and the second image data so as to decrease a difference in resolution between the first image data and the second image data.

11. The photoacoustic apparatus according to claim 1, further comprising:
- a light irradiation unit configured to irradiate the object with the first light and the second light;
- a reception unit configured to output a signal group by receiving photoacoustic waves generated by a first light irradiation with the first light and a second light irradiation with the second light a plurality of times each,
wherein the processing unit is configured to
generate the first image data on the basis of the signal group, and
generate the second image data on the basis of the signal group.

12. A photoacoustic apparatus comprising a processing unit configured to:
obtain a signal group resulting from acoustic waves generated by separately irradiating an object with a first light having a first wavelength and a second light having a second wavelength different from the first wavelength;
perform normalization processing on the signal group so as to decrease a difference in an image characteristic between first image data corresponding to the first wavelength and second image data corresponding to the second wavelength, the first image data being obtained based on the signal group, the second image data being obtained based on the signal group;
generate the first image data and the second image data on the basis of the signal group subjected to the normalization processing; and
obtain position shift information associated with a plurality of irradiation timings of the first light and the second light on the basis of the first image data and the second image data.

13. An information processing method comprising:
obtaining first image data generated based on an acoustic wave generated by irradiating an object with a first light having a first wavelength;
obtaining second image data generated based on an acoustic wave generated by irradiating the object with a second light having a second wavelength different from the first wavelength;
performing normalization processing on at least one of the first image data and the second image data so as to decrease a difference in an image characteristic between the first image data and the second image data; and
obtaining position shift information associated with a plurality of irradiation timings of the first light and the second light on the basis of the first and second image data at least one of which is subjected to the normalization processing.

14. An information processing method comprising:
obtaining a signal group resulting from acoustic waves generated by separately irradiating an object with a first light having a first wavelength and a second light having a second wavelength different from the first wavelength;
performing normalization processing on the signal group so as to decrease a difference in an image characteristic between first image data based on the first wavelength and second image data based on the second wavelength, the first image data being obtained based on the signal group, the second image data being obtained based on the signal group;
generating the first image data and the second image data on the basis of the signal group subjected to the normalization processing; and
obtaining position shift information associated with a plurality of irradiation timings of the first light and the second light on the basis of the first image data and the second image data.

15. A non-transitory computer readable storage medium storing a program for causing a computer to perform an information processing method, the information processing method comprising:
obtaining first image data generated based on an acoustic wave generated by irradiating an object with a first light having a first wavelength;
obtaining second image data generated based on an acoustic wave generated by irradiating the object with a second light having a second wavelength different from the first wavelength;
performing normalization processing on at least one of the first image data and the second image data so as to decrease a difference in an image characteristic between the first image data and the second image data; and
obtaining position shift information associated with a plurality of irradiation timings of the first light and the second light on the basis of the first and second image data at least one of which is subjected to the normalization processing.

* * * * *